US012736054B2

(12) United States Patent
Gross-Hardt et al.

(10) Patent No.: US 12,736,054 B2
(45) Date of Patent: Sep. 15, 2026

(54) NON-OCCLUDING INTRAVASCULAR BLOOD PUMP PROVIDING REDUCED HEMOLYSIS

(71) Applicant: Procyrion, Inc., Houston, TX (US)

(72) Inventors: Sascha Gross-Hardt, Aachen (DE); Tim Kaufmann, Aachen (DE); William L. Clifton, Houston, TX (US); Benjamin A. Hertzog, Houston, TX (US); Jason J. Heuring, Houston, TX (US)

(73) Assignee: Procyrion, Inc., Houston, TX (US)

( * ) Notice: Subject to any disclaimer, the term of this patent is extended or adjusted under 35 U.S.C. 154(b) by 0 days.

(21) Appl. No.: 18/781,873

(22) Filed: Jul. 23, 2024

(65) Prior Publication Data

US 2025/0020127 A1 Jan. 16, 2025

Related U.S. Application Data

(63) Continuation of application No. 17/588,991, filed on Jan. 31, 2022, now Pat. No. 12,078,192, which is a (Continued)

(51) Int. Cl.
*F04D 3/02* (2006.01)
*A61M 60/135* (2021.01)
(Continued)

(52) U.S. Cl.
CPC ............ *F04D 3/02* (2013.01); *A61M 60/135* (2021.01); *A61M 60/178* (2021.01); (Continued)

(58) Field of Classification Search
CPC ... F04D 29/281; A61M 60/13; A61M 60/135; A61M 60/806; A61M 60/812
See application file for complete search history.

(56) References Cited

U.S. PATENT DOCUMENTS 2,704,516 A 3/1955 Mock et al.
2,896,926 A 7/1959 Chapman
(Continued)

FOREIGN PATENT DOCUMENTS

CN 113769260 12/2021
EP 2388029 11/2011
(Continued)

OTHER PUBLICATIONS

Annamalai et al., "Abdominal Positioning of the Next-Generation Intra-Aortic Fluid Entrainment Pump (Aortix) Improves Cardiac Output in a Swine Model of Heart Failure", Circulation: Heart Failure, Aug. 2018, in 6 pages.
(Continued)

*Primary Examiner* — Kenneth J Hansen
(74) *Attorney, Agent, or Firm* — Knobbe, Martens, Olson & Bear, LLP

(57) ABSTRACT

A non-occluding intravascular pump comprises a shroud providing an inlet for incoming blood flow and an outlet for outgoing blood flow, wherein the shroud is a cylindrical housing; an impeller positioned within shroud, wherein a central axis of the shroud and impeller are shared; a motor coupled to the impeller, wherein the motor rotates the impeller to causes blood to be drawn through the inlet and output to the outlet, and the motor is centrally disposed and shares the central axis with the shroud and the impeller; and a plurality of pillars coupling the motor to the shroud, wherein the pillars secure the shroud in close proximity to the impeller. Various design features of the pump may be optimized to reduce hemolysis, such as, but not limited to, inlet length, impeller design, pillar angle, and outlet design.

20 Claims, 21 Drawing Sheets

Related U.S. Application Data continuation of application No. 15/276,590, filed on Sep. 26, 2016, now Pat. No. 11,235,138.

(60) Provisional application No. 62/233,025, filed on Sep. 25, 2015.

(51) Int. Cl.

| | |
|---|---|
| ***A61M 60/178*** | (2021.01) |
| ***A61M 60/205*** | (2021.01) |
| ***A61M 60/237*** | (2021.01) |
| ***A61M 60/422*** | (2021.01) |
| ***A61M 60/806*** | (2021.01) |
| ***A61M 60/81*** | (2021.01) |
| ***A61M 60/857*** | (2021.01) |
| ***F04D 3/00*** | (2006.01) |
| ***F04D 13/02*** | (2006.01) |
| ***F04D 29/18*** | (2006.01) |
| ***F04D 29/52*** | (2006.01) |
| ***F04D 29/54*** | (2006.01) |
| *A61F 2/06* | (2013.01) |

(52) U.S. Cl.

CPC ........ *A61M 60/205* (2021.01); *A61M 60/237* (2021.01); *A61M 60/422* (2021.01); *A61M 60/806* (2021.01); *A61M 60/81* (2021.01); *A61M 60/857* (2021.01); *F04D 3/005* (2013.01); *F04D 13/02* (2013.01); *F04D 13/021* (2013.01); *F04D 29/181* (2013.01); *F04D 29/528* (2013.01); *F04D 29/548* (2013.01); *A61F 2002/068* (2013.01); *F05D 2240/303* (2013.01); *F05D 2250/52* (2013.01)

(56) References Cited

U.S. PATENT DOCUMENTS 2,935,068 A 5/1960 Donaldson
3,031,973 A 5/1962 Herman
3,288,073 A 11/1966 Pezzillo
3,455,540 A 7/1969 Marcmann
3,510,229 A 5/1970 Smith
3,620,584 A 11/1971 Rosenweig
3,812,812 A 5/1974 Hurwitz
4,127,384 A 11/1978 Fahlvik et al.
4,141,603 A 2/1979 Remmers et al.
4,304,524 A 12/1981 Coxon
4,407,508 A 10/1983 Raj et al.
4,613,329 A 9/1986 Bodicky
4,625,712 A 12/1986 Wampler
4,643,641 A 2/1987 Clausen et al.
4,714,405 A 12/1987 Schaefer et al.
4,753,221 A 6/1988 Kensey et al.
4,846,152 A * 7/1989 Wampler ............ A61M 60/237 600/16
4,900,227 A 2/1990 Trouplin
4,919,647 A 4/1990 Nash
4,944,722 A 7/1990 Carriker et al.
4,957,504 A 9/1990 Chardack
4,969,865 A 11/1990 Hwang et al.
4,994,017 A 2/1991 Yozu
5,007,513 A 4/1991 Carlson
5,147,388 A 9/1992 Yamazaki
5,201,679 A 4/1993 Velte, Jr. et al.
5,207,695 A 5/1993 Trout, III
5,211,546 A 5/1993 Isaacson et al.
5,300,112 A 4/1994 Barr
5,368,438 A 11/1994 Raible
5,393,197 A 2/1995 Lemont et al.
5,405,383 A 4/1995 Barr
5,490,763 A 2/1996 Abrams et al.
5,527,159 A 6/1996 Bozeman, Jr. et al.
5,534,287 A 7/1996 Lukic
5,588,812 A 12/1996 Taylor et al.
5,613,935 A 3/1997 Jarvik
5,660,397 A 8/1997 Holtkamp
5,686,045 A 11/1997 Carter
5,722,930 A 3/1998 Larson, Jr. et al.
5,725,570 A 3/1998 Heath
5,749,855 A 5/1998 Reitan
5,824,070 A 10/1998 Jarvik
5,827,171 A 10/1998 Dobak, III et al.
5,911,685 A 6/1999 Siess et al.
5,921,913 A 7/1999 Seiss
5,947,703 A 9/1999 Nojiri et al.
5,951,263 A 9/1999 Taylor et al.
5,964,694 A 10/1999 Siess et al.
6,007,478 A 12/1999 Siess et al.
6,136,025 A 10/2000 Barbut et al.
6,227,797 B1 5/2001 Watterson et al.
6,245,026 B1 6/2001 Campbell et al.
6,253,769 B1 7/2001 LaFontaine et al.
6,302,910 B1 10/2001 Yamazaki et al.
6,517,315 B2 2/2003 Belady
6,527,699 B1 3/2003 Goldowsky
6,533,716 B1 3/2003 Schmitz-Rode et al.
6,547,519 B2 4/2003 deBlanc et al.
6,585,756 B1 7/2003 Strecker
6,609,883 B2 8/2003 Woodard et al.
6,616,323 B2 9/2003 McGill
6,638,011 B2 10/2003 Woodard et al.
6,645,241 B1 11/2003 Strecker
6,660,014 B2 12/2003 Demarais et al.
6,716,189 B1 4/2004 Jarvik et al.
6,733,459 B1 5/2004 Atsumi
6,749,598 B1 6/2004 Keren et al.
6,860,713 B2 3/2005 Hoover
6,866,805 B2 3/2005 Hong et al.
6,887,215 B2 5/2005 McWeeney
6,972,956 B2 12/2005 Franz et al.
7,011,620 B1 3/2006 Seiss
7,125,376 B2 10/2006 Viole et al.
7,189,260 B2 3/2007 Harvath et al.
7,303,526 B2 12/2007 Sharkey et al.
7,374,531 B1 5/2008 Kantrowitz
7,381,034 B2 6/2008 Shishido
7,393,181 B2 7/2008 McBride et al.
7,396,327 B2 7/2008 Morello
7,473,220 B2 1/2009 Francese et al.
7,534,258 B2 5/2009 Gomez et al.
7,682,673 B2 3/2010 Houston et al.
7,758,806 B2 7/2010 Zhao
7,762,941 B2 7/2010 Jarik
7,841,976 B2 11/2010 McBride et al.
7,878,967 B1 2/2011 Khanal
7,914,436 B1 3/2011 Kung
7,993,259 B2 8/2011 Kang et al.
7,998,054 B2 8/2011 Bolling
8,012,079 B2 9/2011 Delgado, III
8,088,059 B2 1/2012 Jarvik
8,123,669 B2 2/2012 Siess et al.
8,177,703 B2 5/2012 Smith et al.
8,403,824 B2 3/2013 Foster
8,579,858 B2 11/2013 Reitan et al.
8,591,393 B2 11/2013 Walters et al.
8,597,170 B2 12/2013 Walters et al.
8,641,594 B2 2/2014 LaRose et al.
8,727,959 B2 5/2014 Reitan et al.
8,731,664 B2 5/2014 Foster et al.
8,734,508 B2 5/2014 Hastings et al.
8,777,832 B1 7/2014 Wang et al.
8,992,407 B2 3/2015 Smith et al.
9,138,517 B2 9/2015 Garrigue
9,138,518 B2 9/2015 Campbell et al.
9,144,638 B2 9/2015 Zimmermann et al.
9,162,018 B2 10/2015 Foster
9,199,020 B2 12/2015 Siess
9,265,870 B2 2/2016 Reichenbach et al.
9,364,593 B2 6/2016 McBride et al.
9,415,147 B2 8/2016 Akkerman et al.
9,433,713 B2 9/2016 Corbett et al.
9,486,566 B2 11/2016 Siess

(56) References Cited

U.S. PATENT DOCUMENTS 9,533,084 B2 1/2017 Siess et al.
9,572,915 B2 2/2017 Heuring et al.
9,616,159 B2 4/2017 Anderson et al.
9,744,281 B2 8/2017 Siegenthaler
9,759,222 B2 9/2017 Zimmermann et al.
9,777,732 B2 10/2017 LaRose et al.
9,907,890 B2 3/2018 Muller
9,919,089 B2 3/2018 Garrigue
10,039,873 B2 8/2018 Siegenthaler
10,111,994 B2 10/2018 Wu et al.
10,195,324 B2 2/2019 Foster
10,201,645 B2 2/2019 Muller
10,413,648 B2 9/2019 Delgado, III
10,443,738 B2 10/2019 Durst et al.
10,722,627 B1 7/2020 Obeid et al.
11,235,138 B2 2/2022 Gross-Hardt et al.
11,241,569 B2 2/2022 Delgado
11,324,940 B2 5/2022 Earles et al.
11,325,138 B2 5/2022 Gross-Hardt et al.
11,351,359 B2 6/2022 Clifton et al.
11,452,859 B2 9/2022 Earles et al.
11,471,665 B2 10/2022 Clifton et al.
11,517,736 B2 12/2022 Earles et al.
11,571,559 B2 2/2023 Clifton et al.
11,642,511 B2 5/2023 Delgado
11,697,017 B2 7/2023 Clifton et al.
11,745,005 B2 9/2023 Delgado, III
11,779,751 B2 10/2023 Earles et al.
11,857,777 B2 1/2024 Earles et al.
12,017,060 B2 6/2024 Clifton et al.
12,078,192 B2 9/2024 Gross-Hardt et al.
12,161,854 B2 12/2024 Earles et al.
12,390,633 B2 8/2025 Stotz
2002/0018713 A1 2/2002 Woodard et al.
2002/0151761 A1 10/2002 Viole et al.
2002/0169413 A1 11/2002 Keren et al.
2003/0105383 A1 6/2003 Barbut et al.
2003/0144574 A1 7/2003 Heilman et al.
2003/0176912 A1 9/2003 Chuter et al.
2003/0233143 A1 12/2003 Gharib et al.
2004/0044266 A1 3/2004 Siess et al.
2004/0046466 A1 3/2004 Siess et al.
2004/0215050 A1 10/2004 Morello
2005/0131271 A1 6/2005 Benkowski et al.
2005/0220636 A1 10/2005 Henein et al.
2006/0036127 A1* 2/2006 Delgado, III ....... A61M 60/139 600/16
2006/0062672 A1 3/2006 McBride et al.
2006/0155159 A1 7/2006 Melvin
2007/0004959 A1 1/2007 Carrier et al.
2007/0156006 A1 7/2007 Smith et al.
2007/0208290 A1 9/2007 Pecor et al.
2008/0103591 A1 5/2008 Siess
2009/0093764 A1 4/2009 Pfeffer et al.
2009/0149950 A1 6/2009 Wampler
2010/0041939 A1* 2/2010 Siess .................. A61M 60/422 600/16
2010/0174131 A1 7/2010 Foster et al.
2010/0249489 A1 9/2010 Jarvik
2010/0256506 A1 10/2010 Mohl
2011/0106115 A1 5/2011 Haselby et al.
2011/0152999 A1 6/2011 Hastings et al.
2011/0160844 A1 6/2011 Haselby et al.
2011/0238172 A1 9/2011 Akdis
2011/0303229 A1 12/2011 Najafi et al.
2011/0318204 A1 12/2011 Omori
2012/0029265 A1 2/2012 LaRose et al.
2012/0134832 A1 5/2012 Wu
2012/0172654 A1 7/2012 Bates
2013/0053623 A1 2/2013 Evans et al.
2013/0303831 A1 11/2013 Evans
2014/0128659 A1 5/2014 Heuring et al.
2014/0200664 A1 7/2014 Akkerman et al.
2014/0275722 A1 9/2014 Zimmermann et al.
2014/0275726 A1 9/2014 Zeng
2015/0258260 A1 9/2015 Tuseth
2015/0285258 A1 10/2015 Foster
2015/0364861 A1 12/2015 Lucke et al.
2015/0364863 A1 12/2015 Andrus et al.
2016/0045652 A1 2/2016 Cornen
2016/0045653 A1 2/2016 Siess
2016/0129170 A1 5/2016 Siess
2016/0303299 A1 10/2016 Muller
2016/0346450 A1 12/2016 Akkerman et al.
2017/0014562 A1 1/2017 Liebing
2017/0014653 A1 1/2017 Duffy
2017/0043074 A1 2/2017 Siess
2017/0087288 A1 3/2017 Grob-Hardt et al.
2017/0128644 A1 5/2017 Foster
2017/0188903 A1 7/2017 Bernstein
2017/0197019 A1 7/2017 Tuseth et al.
2017/0216507 A1 8/2017 Kushwaha et al.
2017/0296720 A1 10/2017 Taskin et al.
2017/0340789 A1 11/2017 Bonde et al.
2018/0010608 A1 1/2018 LaRose et al.
2018/0050139 A1 2/2018 Siess et al.
2018/0050140 A1 2/2018 Siess et al.
2018/0050142 A1 2/2018 Dur et al.
2018/0064861 A1 3/2018 Garrique
2018/0154057 A1 6/2018 Barry
2018/0169312 A1 6/2018 Sun
2018/0193543 A1 7/2018 Sun
2018/0228953 A1 8/2018 Siess et al.
2018/0236150 A1 8/2018 Arnold et al.
2018/0296743 A1 10/2018 Siegenthaler
2018/0303991 A1 10/2018 Nusser et al.
2018/0311421 A1 11/2018 Tuseth et al.
2018/0311425 A1 11/2018 Tuseth et al.
2019/0001034 A1 1/2019 Taskin et al.
2019/0060543 A1 2/2019 Khanal et al.
2019/0097353 A1 3/2019 McSweeney
2019/0125948 A1 5/2019 Stanfield et al.
2019/0133599 A1 5/2019 Obermiller et al.
2019/0143018 A1 5/2019 Salahieh et al.
2019/0269840 A1 9/2019 Tuval et al.
2019/0275224 A1 9/2019 Hanson et al.
2019/0290816 A1 9/2019 Petersen
2019/0298902 A1 10/2019 Siess et al.
2019/0328948 A1 10/2019 Salahieh et al.
2019/0334283 A1 10/2019 Di Paola et al.
2019/0358382 A1 11/2019 Delgado, III
2020/0076271 A1 3/2020 Sconzert et al.
2020/0121834 A1 4/2020 Tuseth et al.
2020/0121835 A1 4/2020 Farago et al.
2020/0306434 A1 10/2020 VanCamp et al.
2020/0316277 A1 10/2020 Delgado, III
2020/0316278 A1 10/2020 Delgado
2020/0330666 A1 10/2020 Siess et al.
2020/0368415 A1 11/2020 Antaki
2021/0008264 A1 1/2021 Radman
2021/0046231 A1 2/2021 Weber et al.
2021/0052793 A1 2/2021 Struthers et al.
2021/0060223 A1 3/2021 Weber et al.
2021/0060224 A1 3/2021 Kronstedt et al.
2021/0069393 A1 3/2021 Schauer et al.
2021/0069397 A1 3/2021 Chouinard et al.
2021/0100940 A1 4/2021 Breidall et al.
2021/0162196 A1 6/2021 Georges et al.
2021/0220634 A1 7/2021 Cook
2021/0220636 A1 7/2021 Schauer et al.
2021/0220637 A1 7/2021 Edwards et al.
2021/0260360 A1 8/2021 Georges et al.
2021/0275796 A1 9/2021 Struthers et al.
2021/0346680 A1 11/2021 Vogt et al.
2022/0080179 A1 3/2022 Earles et al.
2022/0080183 A1 3/2022 Earles et al.
2022/0080185 A1 3/2022 Clifton et al.
2022/0249829 A1 8/2022 Edwards et al.
2023/0020104 A1 1/2023 Earles et al.
2023/0256233 A1 8/2023 Clifton et al.
2024/0017052 A1 1/2024 Delgado, III
2024/0075275 A1 3/2024 Earles et al.
2024/0165394 A1 5/2024 Earles et al.

(56) References Cited

U.S. PATENT DOCUMENTS

| | | | |
|---|---|---|---|
| 2024/0173539 | A1 | 5/2024 | Earles et al. |
| 2024/0416109 | A1 | 12/2024 | Clifton et al. |
| 2025/0360303 | A1 | 11/2025 | Fain et al. |

FOREIGN PATENT DOCUMENTS

| | | |
|---|---|---|
| JP | 2014-501554 | 1/2014 |
| JP | 2018-509224 | 4/2018 |
| JP | 2018-528804 | 10/2018 |
| JP | 2019-523110 | 8/2019 |
| JP | 2019-530501 | 10/2019 |
| WO | WO 1998/000185 | 1/1988 |
| WO | WO 00/33446 | 6/2000 |
| WO | WO 01/10342 | 2/2001 |
| WO | WO 02/070039 | 9/2002 |
| WO | WO 03/103745 | 12/2003 |
| WO | WO 2005/016416 | 2/2005 |
| WO | WO 2005/020848 | 3/2005 |
| WO | WO 2009/046779 | 4/2009 |
| WO | WO 2009/091968 | 7/2009 |
| WO | WO 2016/146663 | 9/2016 |
| WO | WO 2017/118738 | 7/2017 |
| WO | WO 2017/165372 | 9/2017 |
| WO | WO 2018/096531 | 5/2018 |
| WO | WO 2019/094963 | 5/2019 |
| WO | WO 2019/173596 | 9/2019 |
| WO | WO 2019/229224 | 12/2019 |
| WO | WO 2021/062565 | 4/2021 |
| WO | WO 2021/062566 | 4/2021 |
| WO | WO 2021/113389 | 6/2021 |
| WO | WO 2021/117021 | 6/2021 |
| WO | WO 2021/119413 | 6/2021 |
| WO | WO 2021/138673 | 7/2021 |
| WO | WO 2022/256333 | 12/2022 |
| WO | WO 2024/123924 | 6/2024 |
| WO | WO 2025/255135 | 12/2025 |

OTHER PUBLICATIONS

Demirsoy, Ergun et al., Grafting the restenosed coronary artery after removal of multiple failed stents by endarterectomy, Texas Heart Institute Journal, Endarterectomy of Multiple Stents Before Grafts, 2006, vol. 33, No. 2, pp. 262-263.

Greenberg, B., Rationale, Design and Methods for a Pivotal Randomized Clinical Trial of Continuous Aortic Flow Augmentation in Patients with Exacrbation of Heart Failure: The Momentum Trial, Journal of Cardiac Failure, 2007, vol. 13, No. 9, pp. 715-721.

Herzum, M. et al., Managing a complication after direct stenting; removal of a maldeployed stent with rotational artherectomy, Heart Jrnl 2005: 91: e46, URL: http://www.heartjnl.com/cgi/content/full/91/6/e46).

Siess, T. et al., "From a lab type to a product: A retrospective view on Impella's assist technology," Artificial Organs, Jan. 15, 2002, vol. 25, Issue 5, pp. 414-421.

Triantafyllou, K.D. et al., Coronary endarterectomy and stent removal with of-pump coronary artery bypass surgery, Heart Journal, Images in Cardiology, dai: 10.1136/hrt.2005.076687, p. 885.

Vazquez, R. et al., Plasma protein denaturation with graded heat exposure, Perfusion, 2013, vol. 28, No. 6, pp. 557-559.

European Search Report, EP09175307.9, dated Dec. 18, 2009.

Extended European Search Report dated Nov. 27, 2023, European Application No. 20896527.7, 6 pages.

International Search report of PCT/US2005/028875, dated Dec. 16, 2005.

Written Opinion of the International Searching Authority, PCT/US2005/028875, Dec. 15, 2005.

International Search Report and Written Opinion for PCT/US2013/033894, dated Jun. 17, 2013.

International Search Report and Written Opinion issued in PCT Application No. PCT/US2020/064489, dated Apr. 8, 2021, in 26 pages.

International Search Report and Written Opinion issued in PCT Application No. PCT/US2020/062928, dated Apr. 9, 2021, in 26 pages.

Notice of Allowance mailed Oct. 1, 2021, in U.S. Appl. No. 15/276,590, 14 pages.

Supplementary European Search Report dated Jan. 17, 2024, European Application 20900622.0, 8 pages.

* cited by examiner

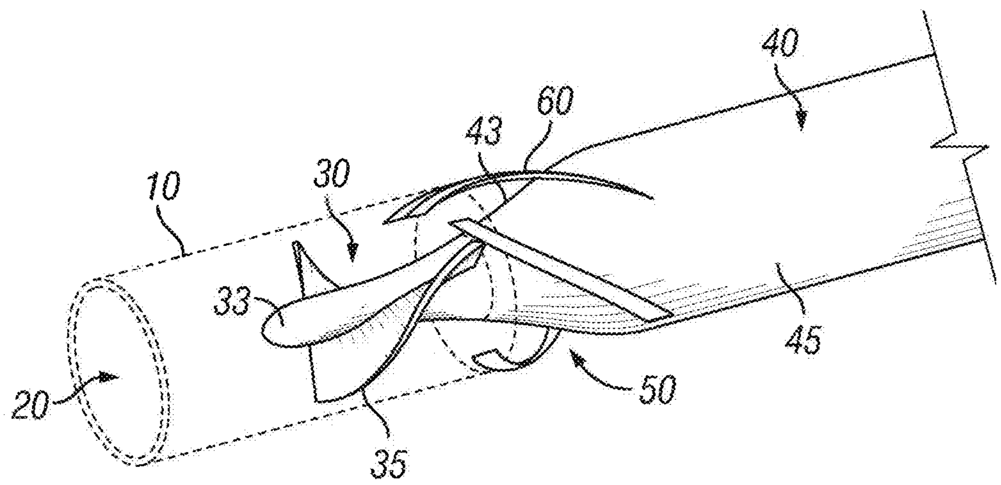
FIG. 1
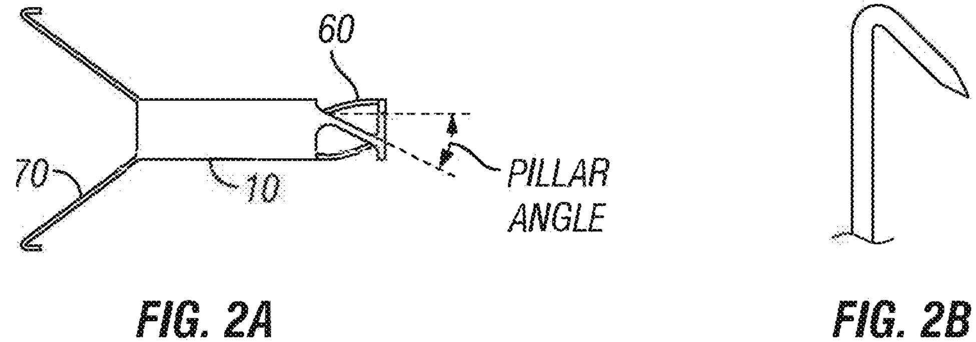
FIG. 2A
FIG. 2B
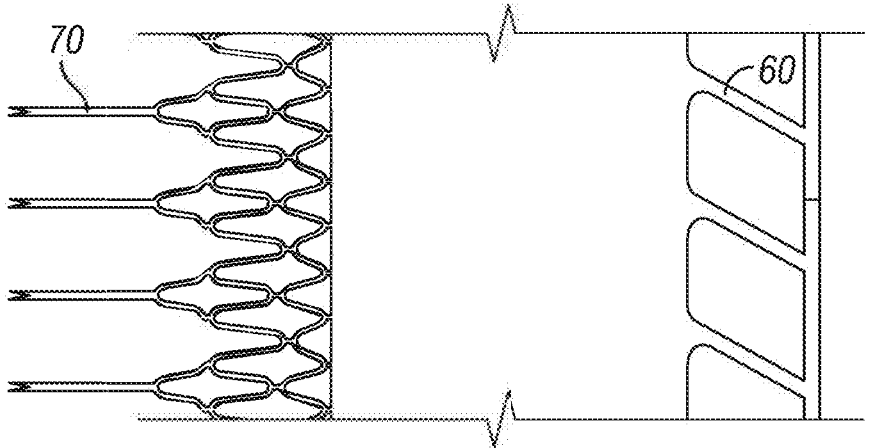
FIG. 2C

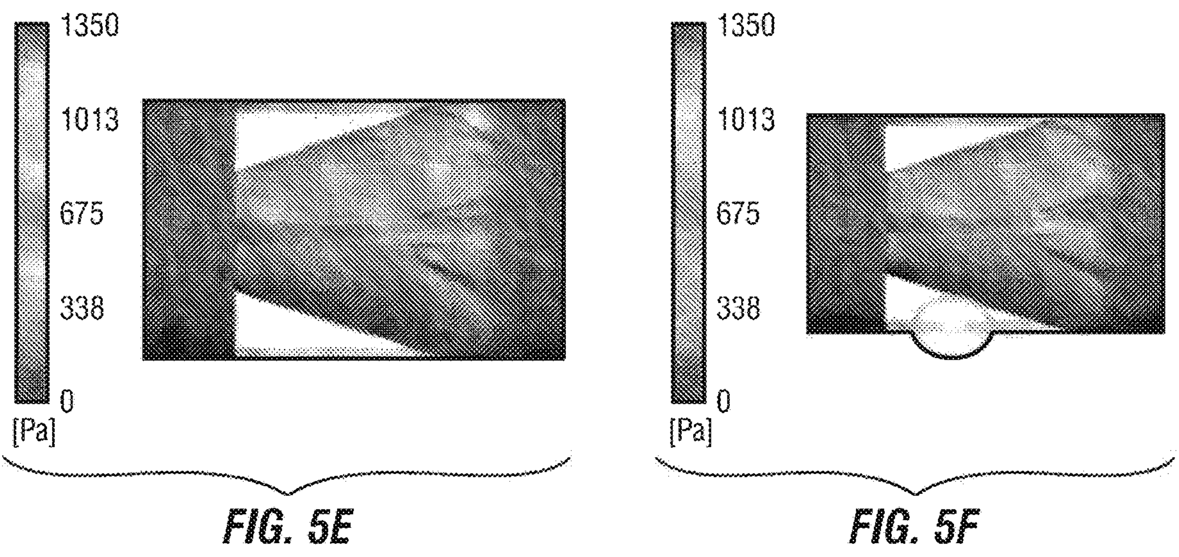
FIG. 5E
FIG. 5F
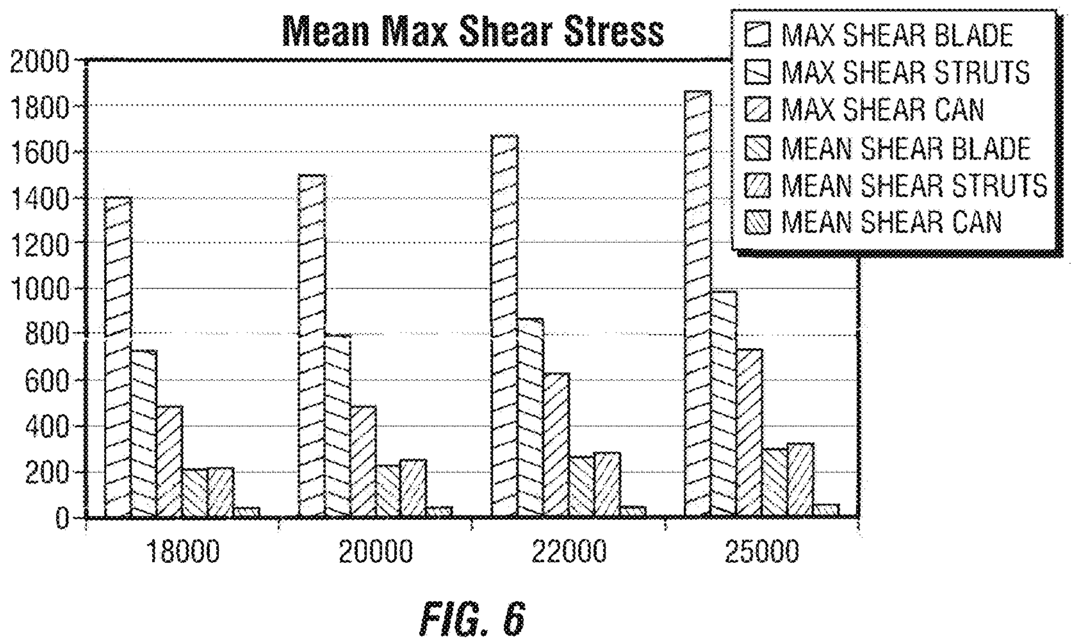
FIG. 6

| PROTOTYPE | $D_{Hb}$_HEUSER | MEAN t |
|---|---|---|
| **P_REF** | | |
| 18k | 1.0418e-05 | 1.246 |
| 20k | 1.1831e-05 | 1.176 |
| 22k | 1.2514e-05 | 1.105 |
| 25k | 1.3024e-05 | 1.014 |
| **P31** | | |
| 18k | 8.6735e-06 | 1.261 |
| 20k | 9.9394e-06 | 1.180 |
| 22k | 1.1531e-05 | 1.107 |
| 25k | 1.2461e-05 | 0.983 |

NON-OCCLUDING INTRAVASCULAR BLOOD PUMP PROVIDING REDUCED HEMOLYSIS

RELATED APPLICATIONS

This application is a continuation of U.S. application Ser. No. 17/588,991, filed Jan. 31, 2022, which is a continuation of U.S. application Ser. No. 15/276,590, filed Sep. 26, 2016, now U.S. Pat. No. 11,235,138, which claims the benefit of U.S. Provisional Patent Application No. 62/233,025 filed on Sep. 25, 2015, the entire contents of each of which are incorporated herein by reference.

FIELD OF THE INVENTION

This invention relates to an improved non-occluding intravascular blood pump providing reduced or minimal hemolysis.

BACKGROUND OF INVENTION

Blood pumps may exert stresses on blood that cause hemolysis or blood clotting. A blood pump may provide an inlet, housing, impeller, outlet, and motor. There may be various hotspots in a pump's design of such components that may exert high stress on blood that can cause hemolysis or blood clotting. In addition to health risk associated with hemolysis and blood clotting, these factors may also impair operation of the blood pump. An example of a blood pump can be found in U.S. Pat. No. 8,012,079.

The improved non-occluding intravascular blood pump systems and methods discussed herein reduce and minimize shear forces that can cause hemolysis or blood clotting.

SUMMARY OF INVENTION

In one embodiment, a non-occluding intravascular blood pump comprises a shroud providing an inlet for incoming blood flow and an outlet for outgoing blood flow, wherein the shroud is a cylindrical housing; an impeller positioned within shroud, wherein a central axis of the shroud and impeller are shared; a motor coupled to the impeller, wherein the motor rotates the impeller to cause blood to be drawn through the inlet and output to the outlet, and the motor is centrally disposed and shares the central axis with the shroud and the impeller; and a plurality of pillars coupling the motor to the shroud, wherein the pillars secure the shroud in close proximity to the impeller. The pump may further provide a variety of design features to reduce hemolysis, such as, but not limited to a trumpeted shroud with a larger inlet than outlet; raking back the leading edge of the impeller blades; a large inlet length to reduce turbulent flow prior to the impeller; a large bare hub length; matching the pillar angle to the outlet blade angle; matching flare angles for the impeller base and stator tip; a desired clearance between the shroud and impeller blades, a desired wrap angle, and any combinations thereof.

The foregoing has outlined rather broadly various features of the present disclosure in order that the detailed description that follows may be better understood. Additional features and advantages of the disclosure will be described hereinafter.

BRIEF DESCRIPTION OF THE DRAWINGS

For a more complete understanding of the present disclosure, and the advantages thereof, reference is now made to the following descriptions to be taken in conjunction with the accompanying drawings describing specific embodiments of the disclosure, wherein:

FIG. 1 shows an illustrative example of a blood pump;

FIGS. 2*a*-2*c* show multiple view of an illustrative example of a shroud;

FIGS. 5*a*-5*f* show hotspots for various components of the pump;

FIG. 6 show mean/max sear stress for the shroud, blade and pillars;

DETAILED DESCRIPTION

Figure 3A:
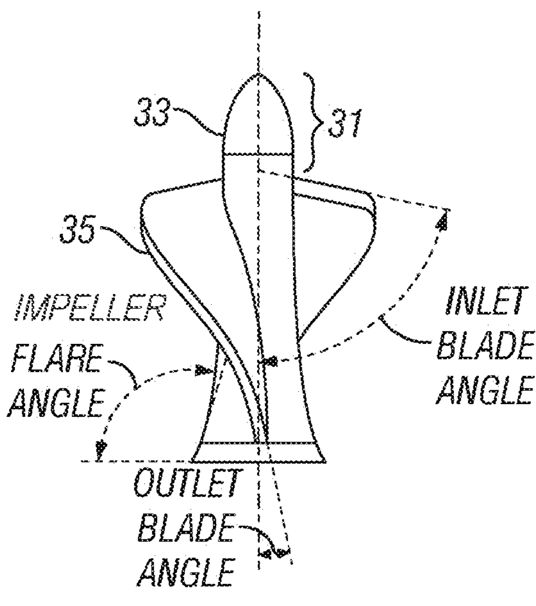
FIGS. 3*a*-3*c* show multiple view of an illustrative example of an impeller.

Refer now to the drawings wherein depicted elements are not necessarily shown to scale and wherein like or similar elements are designated by the same reference numeral through the several views.

Referring to the drawings in general, it will be understood that the illustrations are for the purpose of describing particular implementations of the disclosure and are not intended to be limiting thereto. While most of the terms used herein will be recognizable to those of ordinary skill in the art, it should be understood that when not explicitly defined, terms should be interpreted as adopting a meaning presently accepted by those of ordinary skill in the art.

It is to be understood that both the foregoing general description and the following detailed description are exemplary and explanatory only, and are not restrictive of the invention, as claimed. In this application, the use of the singular includes the plural, the word "a" or "an" means "at least one", and the use of "or" means "and/or", unless specifically stated otherwise. Furthermore, the use of the term "including", as well as other forms, such as "includes" and "included", is not limiting. Also, terms such as "element" or "component" encompass both elements or components comprising one unit and elements or components that comprise more than one unit unless specifically stated otherwise.

In an improved system, the components of a non-occluding intravascular blood pump are designed to reduce or minimize hemolysis. In some embodiments, the blood pump may be a ventricular assist device or an axial blood pump. In some embodiments, the non-occluding intravascular blood pump may provide a shroud, impeller, and flow stator.

FIG. 1 is an illustrative embodiment of a non-occluding intravascular blood pump. In some embodiments, the non-occluding intravascular blood pump may be an axial blood pump with impeller 30 positioned within a shroud 10. Notably the central axis of the shroud 10 and impeller 30 are shared, and this central axis may be referred to as the central axis of the device or pump as it is shared by several components. A shroud 10 may be a generally cylindrical housing for the impeller 30. The shroud 10 may provide an inlet 20 for incoming blood flow and outlet for outgoing blood flow. The device is described as intravascular because it is designed to operate in a blood vessel of the human body. In some embodiments, the central axis of the pump is roughly aligned with the central axis of the blood vessel. The device is non-occlusive because blood flowing in the blood vessel can flow freely around the device. The impeller 30 is coupled to and rotated by motor 40, which causes blood to be drawn through the inlet 20 and forced out the outlet 50. The motor 40 is also centrally disposed and shares the central axis with the shroud 10 and impeller 30. The impeller 30 may include a hub 33 that is central part of the impeller. The blades or vanes 35 of the impeller 30 may be attached to the hub 33. The motor 40 may include a rotor (not shown), stator 43, and motor body 45. Because the motor 40 is centrally disposed and shares the central axis with the shroud 10 and impeller 30, outgoing blood flow from the outlet 50 is diverted around the motor 40. In order to maintain a desired position relative to the motor 40, the shroud 10 may be coupled to the motor 40 with one or more pillars 60. As the motor 40 is coupled to the impeller 30, the pillars 60 may also secure the shroud 10 in close proximity to impeller. As noted previously above, there are several regions or hotspots of such a device that can create stress that may lead to hemolysis.

Further features of a non-occluding intravascular blood pump are discussed herein for illustrative purposes. Due to the complex interaction of various factors that influence flow it shall be understood that parameters discussed herein are for illustrative purposes only and shall not be construed as limiting examples. Thus, any parameters, such as lengths, diameters, distances, angles, or like for the various components of the device shall be understood to be nonlimiting examples, and such parameters may vary slightly from values discussed below (e.g. +/−10%). It shall also be understood that each of the variety of embodiments discussed herein may be suitable for combination with one or more other embodiments.

FIGS. 2*a*-2*c* show multiple view of an illustrative example of a shroud 10, more particularly, a formed shroud, an enlarged view of a strut tip, and a pre-assembled flat view respectively. In some embodiments, the shroud 10 may be integrated with struts 70 that may be utilized to secure the device in a desired location of the circulatory system in a patient. As shown in the enlarged view of the strut tip, the tip may be hook and pointed to aid secure placement (e.g. Tine bend angle=) 135°. As shown in the flat view, in some embodiments, the shroud 10 may be formed by patterning (e.g. laser patterning) a desired material to provide struts 70 and pillars 60, and subsequently rolled to form the desired cylindrical shape. The shroud material may be any suitable material (e.g. NiTi or nitinol).

In some embodiments, design aspects of the shroud 10 that are of interest for reducing hemolysis may include the shroud inlet shape. In some embodiments, the shroud 10 may be trumpeted. In particular, the shroud inlet may provide a larger inlet in comparison to the outlet. As a nonlimiting example, the shroud may be trumpeted such that an inlet diameter is larger than an outlet diameter. As discussed further below, this trumpeted design may minimize flow turbulence into the pump at the inlet.

Additionally, various parameters of the shroud 10 may also influence performance, including the shroud inlet length, inlet to blade angle matching, wrap angle, or combinations of these various parameters. In some embodiments, a shroud inlet length is long enough to prevent turbulent flow detachment. The shroud inlet length is defined as a length from the inlet to a tip of the impeller. In some embodiments, the necessary length may be a function of the shroud diameter, the inlet blade angle, the wrap angle, and/or impeller speed. As a nonlimiting example, in the embodiment explored, a shroud inlet length of 9 mm or greater was sufficient to prevent detachment. In some embodiments, a shroud inlet length of at least 1.5 times the inner diameter of the shroud is sufficient to provide good flow conditions for the impeller. In some embodiments, a shroud inlet length of at least 0.5 times the inner diameter of the shroud is included to be sufficient to provide good flow conditions for the impeller. In some embodiments, a shroud inlet length of 0.5 to 1.5 times the inner diameter of the shroud is included to be sufficient to provide good flow conditions for the impeller. Optimal dimensions may depend on native flow conditions.

Figure 3B:
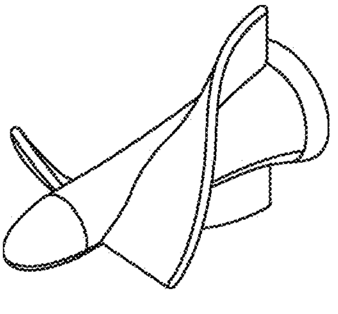
Figure 3C:
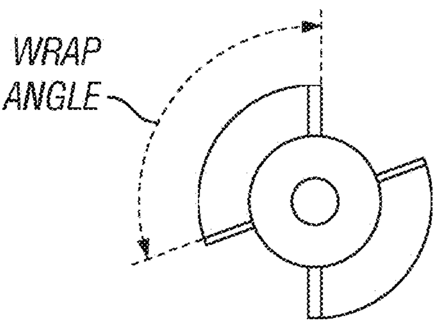
Figure 4A:
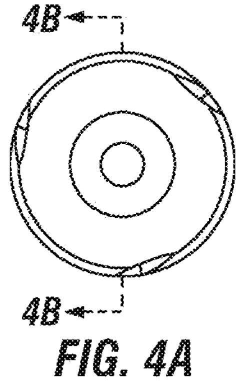
FIGS. 4*a*-4*e* show multiple view of an illustrative example of a stator.
Figure 4B:
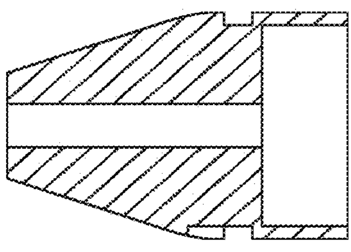
Figure 4C:
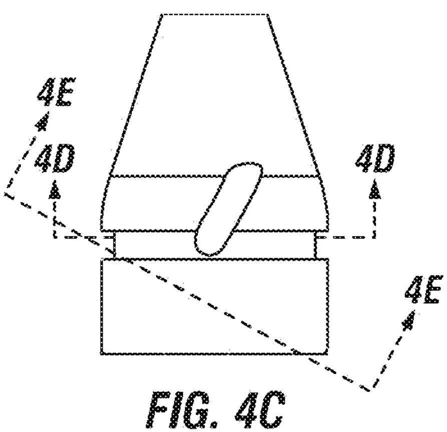
Figure 4D:
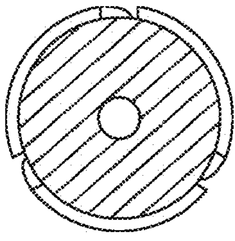
Figure 4E:
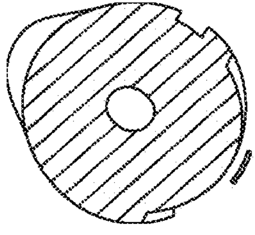
Figures 5A, 5B, 5C, 5D:
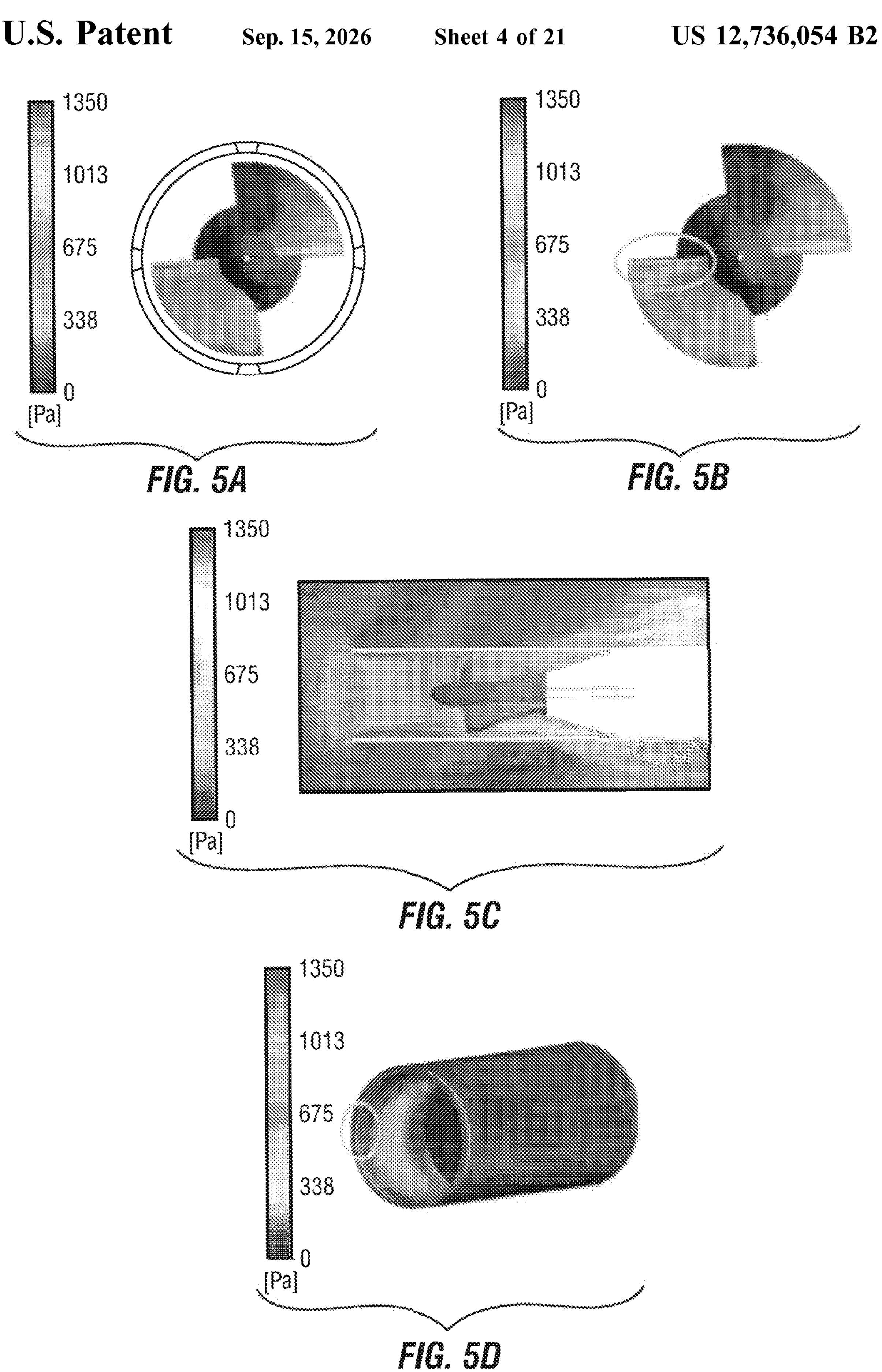

FIGS. 3*a*-3*c* show multiple view of an illustrative example of an impeller. More particularly, a side view, isometric view, and top view of the impeller. As discussed previously, the impeller is positioned on the central axis of the pump and rotates about the central axis when driven by the motor. The hub 33 refers to the central portion of the impeller and may be selected from any suitable blunted or truncated cone design (e.g. spherical, elliptical, parabolic, etc.) The bare hub or hub tip 31 is a portion of the tip of the impeller before blade attachment or a length from the tip of the hub 33 to the beginning of the blades 35. The length of the hub tip 31 should be selected to provide beneficial flow results. In some embodiments, a long hub tip 31 is selected to provide laminar flow to the impeller inlet domain area. The necessary length and shape of the bare hub 31 may depend on the inner shroud diameter, the inlet blade angle, the wrap angle, and/or impeller speed. In some embodiments, a bare hub length of at least 0.3 times the inner diameter of the shroud may be sufficient to provide good flow matching between the inlet flow and the impeller. In some embodiments, a bare hub length of at least 0.2 times the inner diameter of the shroud may be sufficient to provide good flow matching between the inlet flow and the impeller. In some embodiments, a bare hub length of 0.2 to 0.3 times the inner diameter of the shroud may be sufficient to provide good flow matching between the inlet flow and the impeller. In some embodiments, the bare hub length embodiments discussed herein may be combined with embodiments discussing the shroud inlet length. The inlet blade angle refers to angle of the leading edge of the blade 35 relative to the central axis when measured from the downstream side. It is apparent from figures that the leading edge is the edge of the blade closest to the inlet. In the embodiment explored, a bare hub length of roughly 2 mm, with proper profiling, was sufficient to provide good flow conditions. The wrap angle refers to an angle occupied by a single blades 35 wrapped around the hub when viewed from the perspective of the central axis or an angle around the central axis that the single blade occupies (e.g. FIG. 3*c*). In some embodiments, the wrap angle may be 100+/−10 degrees.

In some embodiments, the leading edges of the blades 35 may be raked back and/or may be sharp, pointed, rounded, or the like. Traditional pumps arrange the leading edge of vanes to extend directly perpendicular to a central axis of the pump. In other words, the leading edges of the impeller vanes typically come straight out from the central axis of the pump or the inlet blade angle of typical impeller vanes is 90°. In some embodiments, the leading edge(s) of the impeller vanes are raked back with respect to the direction of flow so that an inlet blade angle (or leading edge angle or rake angle) between the central axis and leading edge is less than 90° (measured from the downstream side of the leading edge). The proper inlet blade angle may depend on the length and shape of the bare hub and the speed of the pump. In some embodiments, the leading edge(s) of the impeller vanes are raked back so that the leading edge angle is 2:60° and <90°. In certain embodiments, the rake angle should be in the range of 75-85 degrees. In some embodiments, the leading edge(s) of the impeller vanes are raked back more so that an angle between the central axis and leading edge is 60-75 degrees. In some embodiments, the leading edge(s) of the impeller vanes are raked back more so that an angle between the central axis and leading edge is less than 60°.

Referring to FIGS. 2*a*-2*c* and 3*a*-3*c*, the shroud and impeller may be matched. In some embodiments, the shroud-tip clearance or a clearance between the inner surface of the shroud and the vanes 35 of the impeller may be designed to be in a desired range. Necessary clearance values may be related to design tolerances, the diameter of the impeller, and the speed of the pump. As a nonlimiting example, clearances may be set to maintain shear rates below a critical value of 10,000-50,000 s-1. For some embodiments, the clearance distances should be at least 250 microns (+/−50 micron). In some embodiments, the clearance between the interior surface of the shroud and the blades of the impeller may be between 200 microns to 300 microns.

FIGS. 4*a*-4*e* show multiple view of an illustrative example of a stator, which is the stationary part of a motor. In some embodiments, the stator and impeller may be matched. In some embodiments, flaring of stator hub or slope of the stator hub is selected to match the flare at the base of the impeller or the impeller flare angle may be approximately equal to the stator flare angle. An impeller flare angle is an angle between the outer surface of the base of the impeller and line perpendicular to the central axis (e.g. FIG. 3*a*). A stator flare angle is angle between the outer surface of the tip of the stator and line perpendicular to the central axis (e.g. FIG. 4*b*). In some embodiments, the base diameter of the impeller and tip diameter of the stator hub may be approximately equal. In some embodiments, the impeller flare angle may be approximately equal to the stator flare angle, and the base diameter of the impeller and tip diameter of the stator hub may be approximately equal. This provides a smooth transition between the impeller and stator that minimizes disruption in flow.

Referring to FIGS. 2*a*-2*c* and 3*a*-3*c*, the pillars 60 and impeller may be matched. As shown in FIG. 2*a*, a pillar angle is an angle between the pillar 60 and the central axis of the pump. In some embodiments, the pillar angle is non-zero. Referring to FIG. 3*a*, the blade angle or outlet blade angle is an angle of the trail end of the blade relative to the central axis. In some embodiments, the pillars may be curved to match the outlet blade angle to minimize shear stress and resistance and optimize flow path. Due to the complex interaction of various factors that influence flow, the optimal angle move+/−5-10 degrees from an exact matching angle.

In some embodiments, the number of pillars compared to the number of impeller blades may be selected to mismatch. For example, a non-integer ratio of impeller blades to pillars may be selected so that they are not equal or matched. In some embodiments, the alignment of the pillars relative the impeller blades may be selected to mismatch, and may optionally combined with the above noted mismatching of the number of pillars and blades. For example, in a nonlimiting embodiment, the pillar and blade configuration may be selected so that when at least one blade is aligned with one of the pillars, the other remaining blades are not all aligned with the other remaining pillars. For example, three outlet pillars may be provided when two impeller blades are provided. In some embodiments, the pillars may be irregularly spaced. In some embodiments, pillar and blade configurations are selected so that when at least one blade is aligned with one of the pillars, none of the remaining impeller blades align with any of the remaining pillars.

In some embodiments, the device may be a catheter-based circulatory heart pump, such as a pump designed specifically for NYHA Class III-IVa heart failure patients who are too sick for medication alone, but not sick enough for risky surgical interventions (i.e. LVAD or transplant).

The following examples are included to demonstrate particular aspects of the present disclosure. It should be appreciated by those of ordinary skill in the art that the methods described in the examples that follow merely represent illustrative embodiments of the disclosure. Those of ordinary skill in the art should, in light of the present disclosure, appreciate that many changes can be made in the specific embodiments described and still obtain a like or similar result without departing from the spirit and scope of the present disclosure. It should also be noted that the examples discussed below progressed through various phases of testing where the designs remained confidential, as such earlier design phases should not be construed as known prior art.

Some of the challenges in producing an improved non-occluding intravascular blood pump are the numerous design factors that can influence performance. It was found that the best approach to get a feasible design includes seeking a minimally invasive design, high rotational speeds, and adaptation for wide operational range. Detailed flow analysis was performed, particularly transient analysis, which allowed precise prototype comparison and setup. Further discussion below includes discussion of typical hotspots, geometry iterations for impeller and housing, results, and conclusions, including hotspot analysis that enables efficient shear force and hemolysis reduction.

The project progressed through three project phases with the initial phase starting with a basic pump design utilized to identify common design flaws causing hemolysis. Initial challenges of the experiments, particularly project Phase 1 and 2, were to develop hydraulic design, including ~6 mm diameter pump, placement in the descending aorta, and in series operation with the left ventricle. Further, additional goals were to deliver sufficient hydraulic output to increase circulation and decrease the workload of the native heart. Phase 3 goals included achieving the lowest hemolysis possible, while providing a wide off-design operating range, lower speeds, and delivering adequate hydraulic output.

Evaluation strategy included simulation in (physiological) operation environment with validation through pump h-q curves and pressure gradient driven backflow. Pump flow depends strongly on rpm and slightly on output flow & pressure.

The Numerical Setup included simulation of series operation, placement in the descending aorta, pump flow function (rpm), validation of pump performance, hotspot analysis of impeller, including asymmetrical shear pattern, flow exploration in inflow shroud, including turbulent flow detachment, and pillar geometry. FIGS. 5*a*-5*f* show hotspots for various components of the pump.

In order to identify the greatest potential for optimization without sacrificing performance, shear stress hotspot identification was performed. Major localized hotspots were found at the impeller, inflow shroud, and pillars. Pre-analysis included hotspot component quantification. FIG. 6 show mean/max shear stress for the shroud, blade and pillars. It was noted that max shear: Impeller>>Pillars>Shroud, and mean shear: Impeller~Pillars>>Shroud.

Operational range analysis included hotspot screening for wide operation range, particularly for constant speed, imposed mass flows, as well as localized hotspots.

Figure 7:
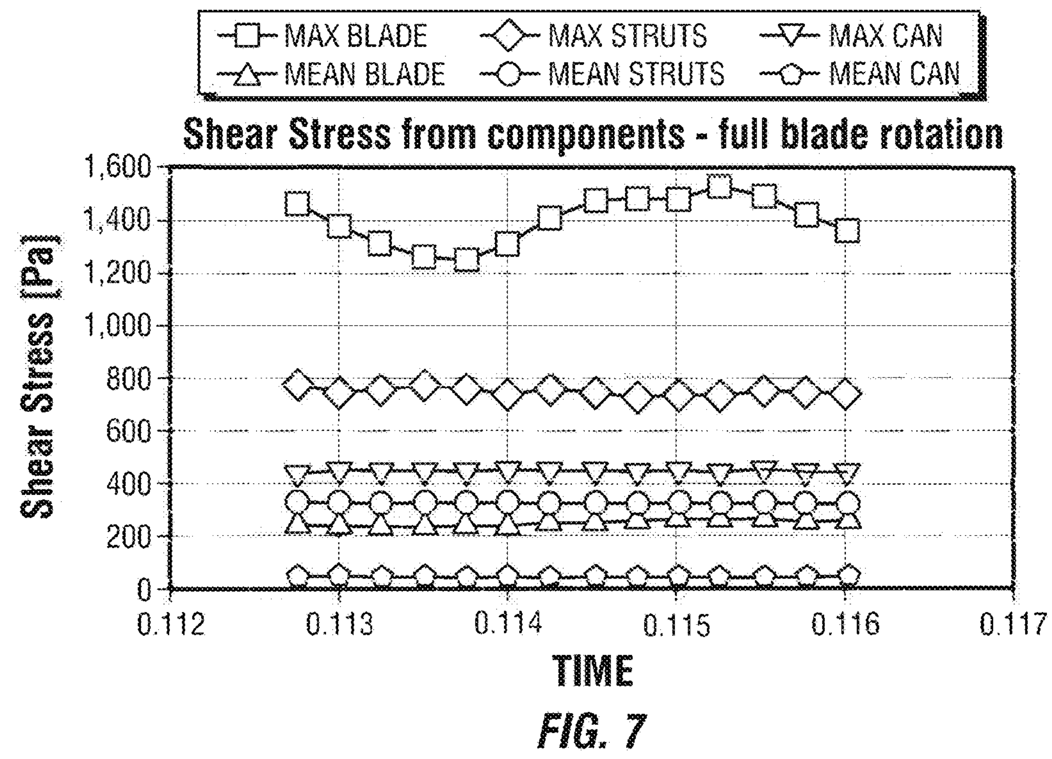
FIG. 7 shows max/mean shear stress for the blade, pillars, and shroud over time.

Prior to the experiments, it was unclear what provokes the asymmetrical shear pattern at the impeller leading edge. An unexpected result was that the detached flow reached as far as the impeller leading edge and provoked the patterns. Transient data was also analyzed to extend the analysis setup. FIG. 7 shows max/mean shear stress for the impeller, pillars, and shroud over time. Transient results were indispensable for optimization, and allowed comparison of mean value and deviation for different designs and identification of geometry flaws that provoke turbulent flows.

Operational range analysis was performed for hotspot screening to determine component contribution to maximum shear stress, shear stress for various rpms, and shear stress for impeller rotation.

Testing showed certain design features may result in improvement:

- Inlet Shroud: an elongated shroud demonstrated the same detachment and symmetric shear at impeller. A smooth inlet transition reduced detachment length of incoming flow at the inlet.
- Impeller: On the upstream portion of the impeller, parameters of interest included the bare hub length. Where the impeller blades join the hub, parameters of interest include leading edge angle and shape (or roundness). Along the bladed portion of the impeller, the parameter of interest was the wrap angle (or blade extent). At the downstream edge of the impeller blades, the parameter of interest was the trailing edge angle or outlet blade angle.
- Outflow Pillars: It was found that edge shape rounding and adjusting pillar tilt angle according to pump outflow angle were important.

Analysis at different scales provided complimentary results. Local prediction showed improved impeller blade surface smoothness resulted in a reduction of maximum (150-200 Pa) and mean shear stress for various RPMs. Global prediction and hotspot analysis enabled improved overall numerically predicted damage index (include time exposure). The analysis show overall improvement for the intended operating range.

Figure 8:
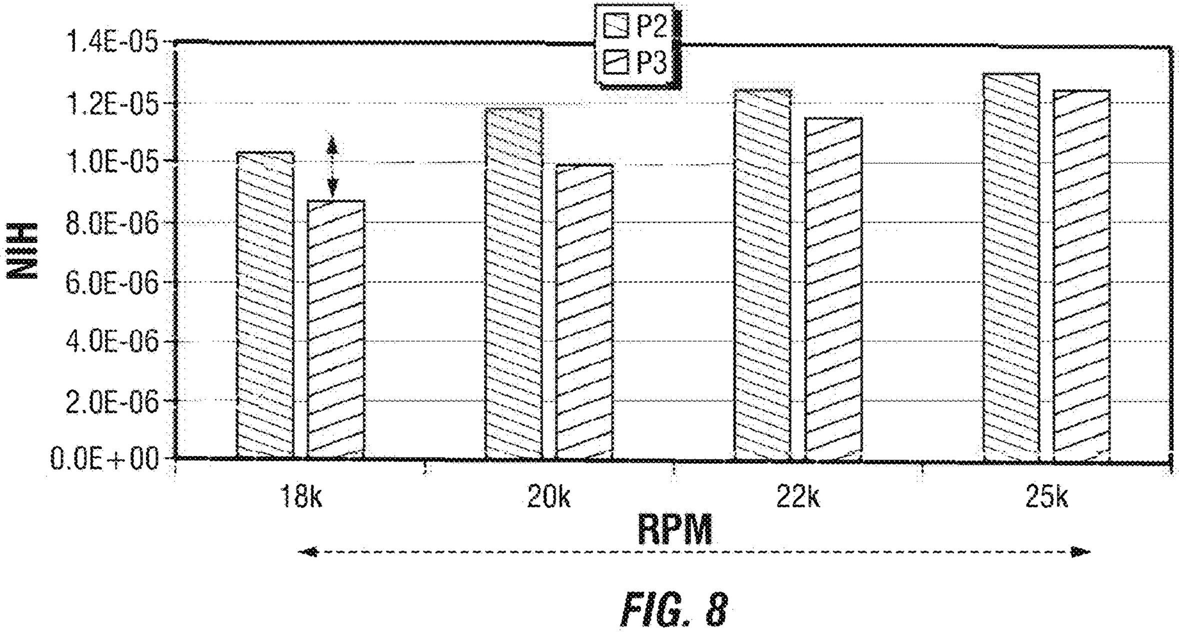
FIG. 8 show the NIH for various rpm for P2 and P3.
Figure 9:
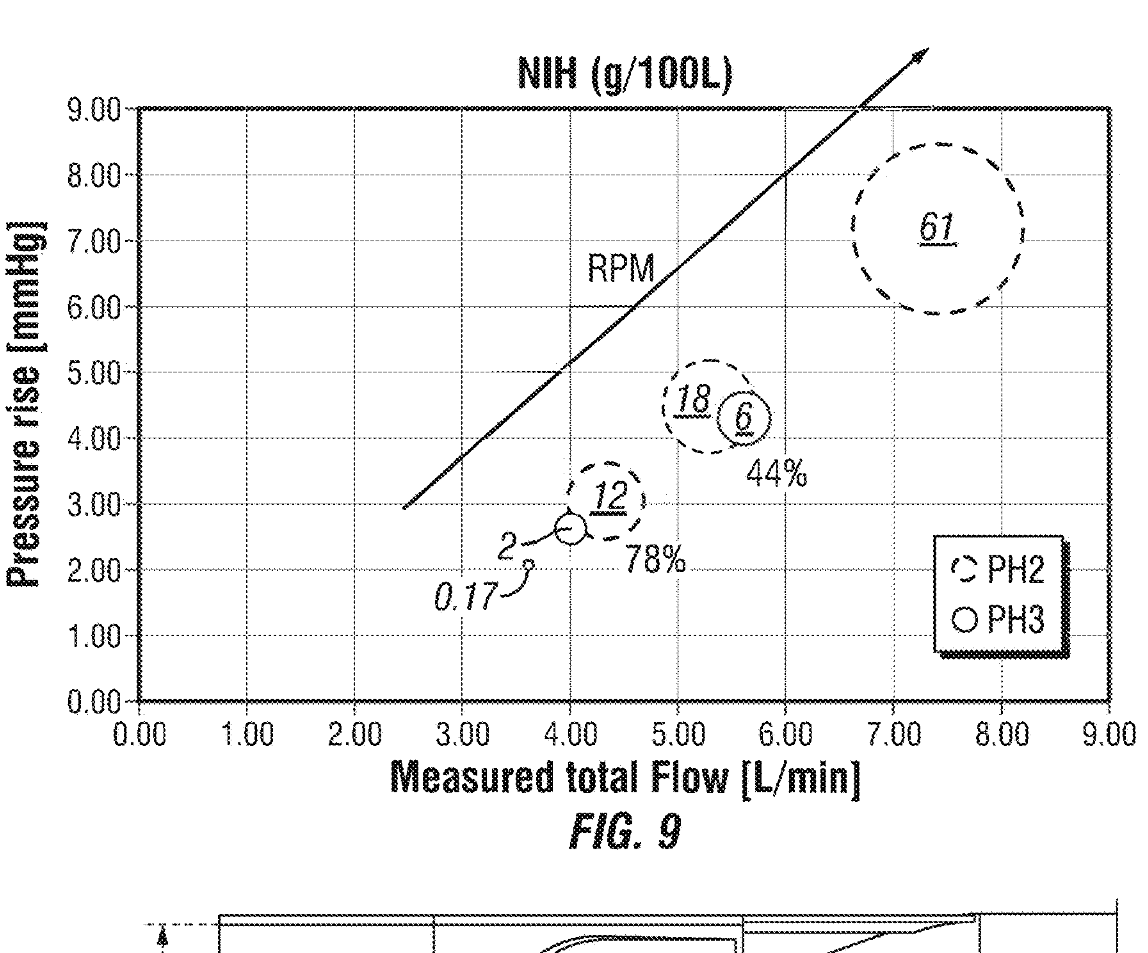
FIG. 9 shows pressure rise v. NIH and measure total flow.

Experimental NIH validation: FIG. 8 shows the NIH for various RPM for P2 and P3, and FIG. 9 shows pressure rise v. NIH and measured total flow. Hotspot analysis enabled improved overall numerically predicted damage index AND experimentally found levels of hemolysis. Experiments show greatly improved hemolysis results as a multiple of BP80 reference pumps.

Conclusion: Thorough hot spot analysis to determine optimization procedures allows one to identify the possible interplay of hotspots, and decide on optimization order(s) to achieve a wide operation range and improved hydraulic output.

The non-occluding intravascular blood pump discussed herein is a minimally invasive continuous axial flow pump (e.g. ~6 mm width) and is especially suited for New York Heart Association (NYHA) Class Ill and early IV patients. The miniaturization of a pump of this type requires high rotational impeller speeds to achieve sufficient unloading of the heart. In order to minimize hemolytic potential of the blood contacting components, a detailed analysis was conducted and iterative optimization of the geometry to design a prototype impeller and blood contacting components. Transient computational fluid dynamic (CFD) simulations over multiple impeller rotational speeds were conducted to determine the time dependent exposure to shear stress, shear stress hotspots, and individual component contribution to hemolysis. The shape of the pump components were iteratively changed to optimize the local flow and shear stress exposure. The final prototype configuration was further numerically evaluated using a conventional Lagrange particle tracking approach accounting for the blood damage accumulation. For validation, in vitro hemolysis testing and flow loop pump performance was conducted. Compared to the initial design, reduction in shear stress and mitigation of hotspots could be achieved. Maximum shear stress exposure could be reduced by 150-200 Pa For the impeller, and average shear on the impeller surface was reduced below 400 Pa up to 30,000 rpm impeller speed. Experimental results of the pump's Normalized Index of Hemolysis (NIH) values showed a significant improvement of 78% at the desired operating speed of 20 k rpm, showing a comparable NIH Level range as the reference pump BP80. Flow Loop performance testing verified that flow rate and pressure generation was maintained following the design changes that resulted in reduction of hemolytic potential. The new prototype features lower numerically predicted and experimentally verified hemolytic potential and increased efficiency through improved overall flow guidance.

In Phase III, a complete analysis of shear stress hotspots within the pump and their individual contribution to hemolysis was conducted. The main focus of this study is the optimization towards lowest possible hemolysis potential by iteratively adapting the blade shape. Furthermore, the whole pump is analyzed for further shear stress hotspots. After identification of the existing shortcomings in the actual prototype impeller operating at the chosen speed range, several shroud and pillar designs are explored. A vast number of different geometries have been created, simulated and analyzed to determine the optimal geometry component fit.

Figure 10:
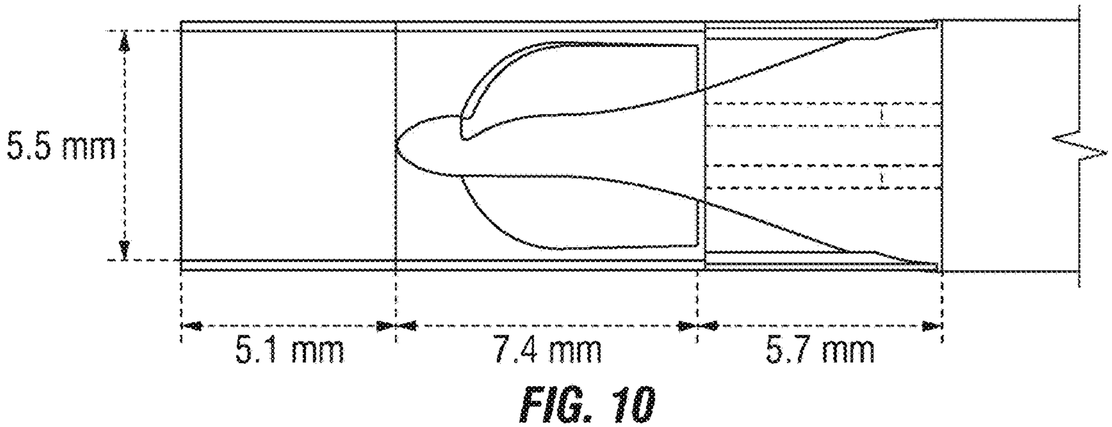
FIG. 10 shows the phase 2 prototype's configuration.

Current Prototype from Phase II: The current prototype (or P_ref) has been identified in an extensive optimization in phase II to lower overall hemolysis potential. FIG. 10 shows the phase 2 prototype's configuration. At that time, the optimal impeller speed was determined to be at 32 k rpm and a significant optimization could be achieved.

P_ref has been evaluated in several hemolysis tests. The main changes conducted in phase II were the iterative adaptation of inlet and outlet blade angle to achieve an overall better flow guidance of the impeller, as well as an increase in wrap angle which allowed a better flow guidance within the blade passage. Furthermore, the shape of the tip hub section has been altered to allow for a more evenly distributed and laminar flow pattern at the impeller inlet region. In the following discussion the further geometry changes to decrease the hemolytic potential of the hotspots identified are presented.

Shroud: An efficient and reliable pump is achieved by a targeted tuning of its components to one another. A perfect example of this was experienced during this study. The shroud length does not significantly lower the shear stress for the component shroud, but eliminates the dependence of blade rotation angle and turbulent flow features on impeller shear stress distribution. The extension of the shroud is necessary to avoid detached turbulent flow reaching into the impeller inlet domain area. This turbulent flow is responsible for the asymmetrical impeller shear stress load and, due to its turbulent random nature, impedes a significant and conclusive optimization of the blade. The results show the impact of detached flow on the shear stress values by having huge oscillation around its mean.

Figure 11:
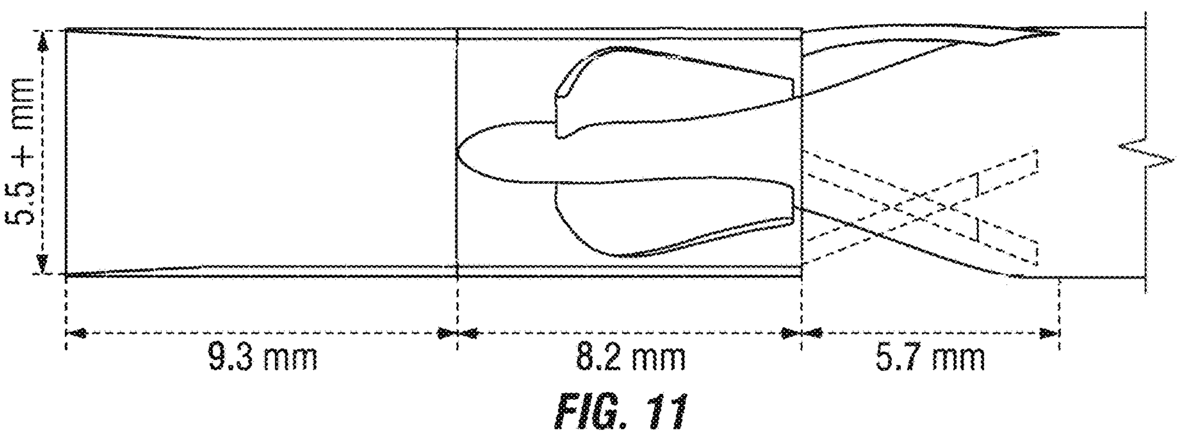
FIG. 11 shows an improved design with geometry data.
Figure 12A:
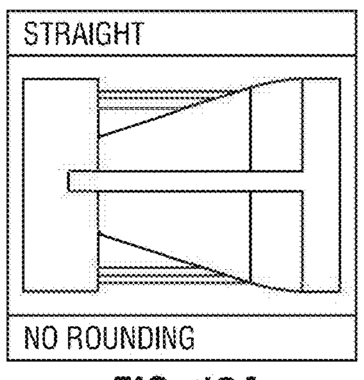
FIGS. 12*a*-12*f* shows selected pillar geometries.
Figure 12B:
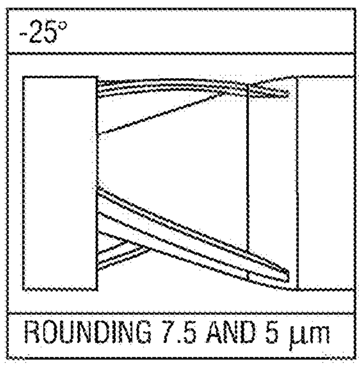
Figure 12C:
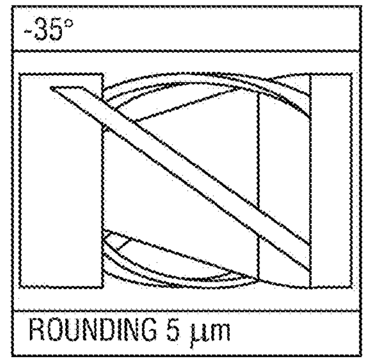
Figure 12D:
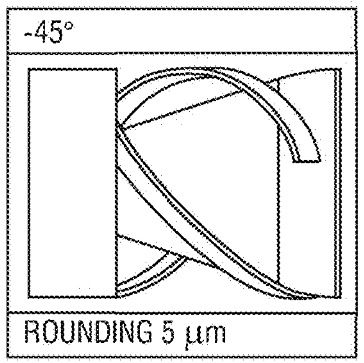
Figure 12E:
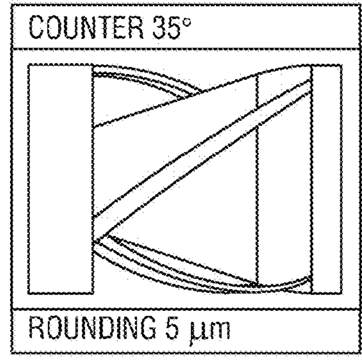
Figure 12F:
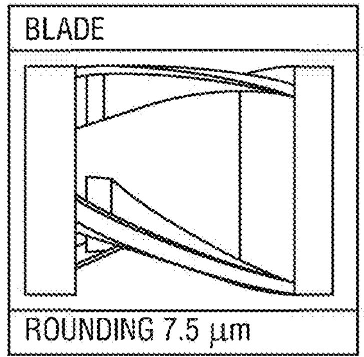
Figure 13A:
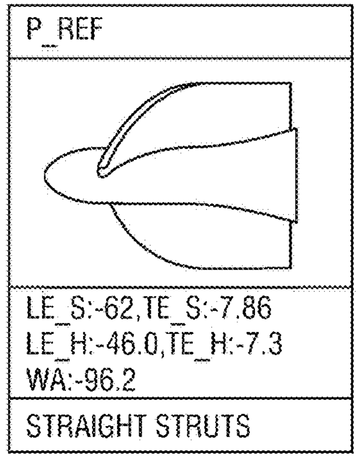
FIGS. 13*a*-13*f* shows selected impeller geometries.
Figure 13B:
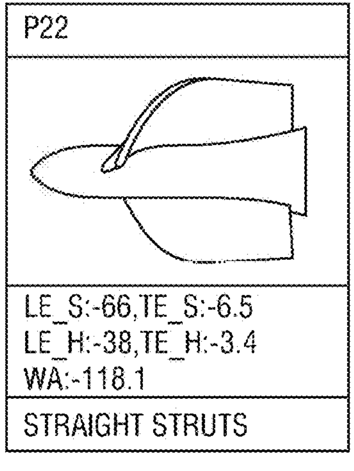
Figure 13C:
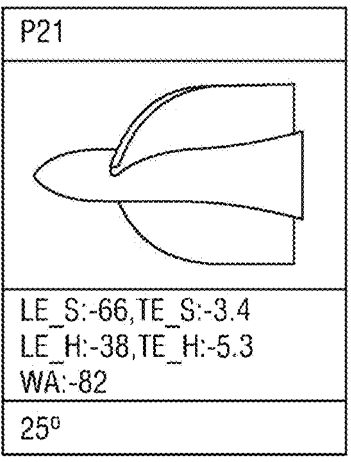
Figure 13D:
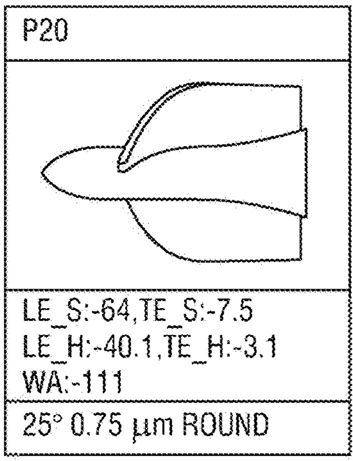
Figure 13E:
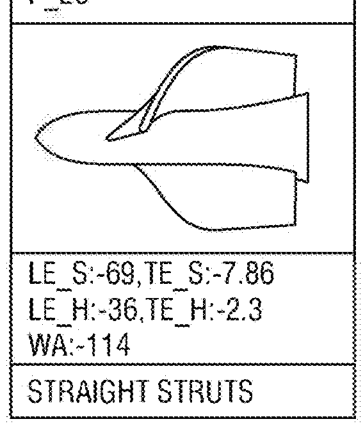
Figure 13F:
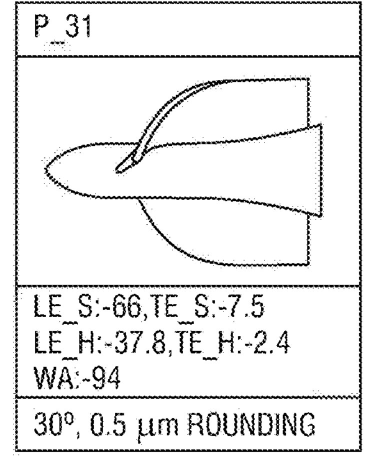
Figure 14A:
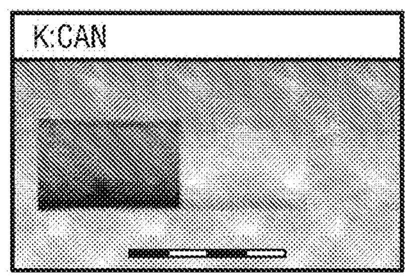
FIGS. 14*a*-14*d* show the individual components and the test surface area evaluated for max and mean shear stress.
Figure 14B:
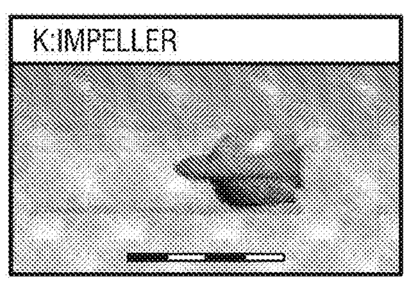
Figure 14C:
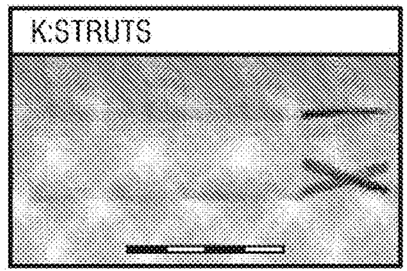
Figure 14D:
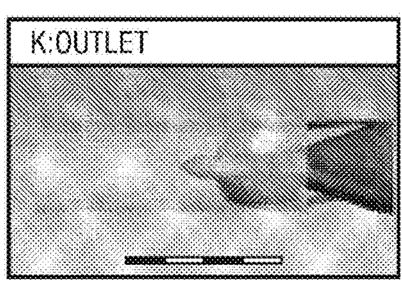

During Phase III, the shroud has therefore been extended; exact data can be found in FIG. 6. FIG. 11 shows an improved design with geometry data. These considerations suggest that an improved pump by extending the shroud length or inlet pipe to allow for sufficient flow settlement, e.g. at least 9.3 mm for the prototype. This can be generalized as at least 1.5 times the shroud inner diameter. Further, a trumpet shape at the inlet is preferred in terms of even earlier flow settlement.

Pillars: The setup from FIG. 11 has been further extended to also record statistics for shroud and pillar stress to capture all shear stresses occurring during 2 blade rotations. Various pillar designs have been modeled and simulated and are explained below. FIGS. 12*a*-12*f* shows selected pillar geometries. The basic idea behind modification of the pillar design is to align the pillars in direction of the outflow jet to minimize the surface area that is directed towards it.

Two main considerations need to be discussed. Due to the orientation of the pillars, the location of the hotspots is affected. A highly twisted pillar design will move the hotspot in the direction of the transition of pillar to motor. In addition, it is assumed that a better aligned pillar compromises less attack surface area and thus reduces the average load. Furthermore, two designs have been created. A counter oriented pillar design at 35°, as well as a stator-pillar component to assess maximum occurring shear stress in relation to mean shear stress.

Impeller: Fifteen independent pump geometry combinations have been simulated to identify the best possible designs and combination. FIGS. 13*a*-13*f* shows selected impeller geometries. Next to the iterative adaptation of the blade angles along the leading edge, a further elongation of the hub showed beneficial impact on changes made to the blade angles. Furthermore, for the same leading edge blade angles, the impact of wrap angle has been investigated as well as a with reference to the hub inclined leading edge.

Blood Damage Prediction: Shear-induced blood trauma (hemolysis) is estimated by computing the damage accumulation along 3000 particle path lines using a Lagrangian particle tracking technique and applying a power-law empirical damage model as suggested by Heuser:

$$D_i = C \times \tau^{\alpha} \times \tau^{\beta}$$

where $D_i$ represents the blood damage index for each particle, C, α and β denote constants originally specified by Giersiepen and later corrected by Heuser as $$C = 1.8 \times 10^{-6},\ \alpha = 1.991,\ \text{and}\ \beta = 0.765.$$

As these coefficients are derived from uniform-shear experiments in Couette-type flow, there are certain limitations to the current problem. However, it is assumed that this does not affect the comparative evaluation of similar pumps. To account for the highly time-variant shear history of blood cells through the pump, the cumulative damage is estimated by the method extended to blood pumps by Bludszuweit (1) based on the assumption of linear accumulation of shear at different loading levels:

$$D_{Hb} = \frac{1}{n} \sum_{inlet}^{outlet} D_i$$

where n is the number of total particles released in the pump inlet, and $D_i$ is calculated using the proposed constants by Heuser. Because of the three-dimensional character of the shear field, the Von Mises stress provides a representative scalar norm for use in calculation of $D_i$, as proposed by Bludszuweit:

$$\tau = \left[\frac{1}{6} \sum (\tau_{ii} + \tau_{ii})^2 + \sum \tau_{ij^2}\right]^{\frac{1}{2}}$$

where the components of the stress tensor were computed from the summation of the components of the viscous and Reynolds stress tensor.

Results: In the course of this project, a huge data set by the evaluation of all configurations prototype was created. To an illustrative comparison, however, only the parameters of comparison of the original and within this project identified final pump geometry are shown below. Furthermore, most graphic results are shown at 20 krpm. Due to the huge amount of created data, only selected configuration results will be shown below. The individual components and the test surface area evaluated for max and mean shear stress are shown in FIGS. 14*a*-14*d*. Surface area K: OUTLET was monitored for every run to make sure that modifications made to the pillars do not somehow impair the shear stress distribution in the whole outlet area of the pump.

Figure 15A:
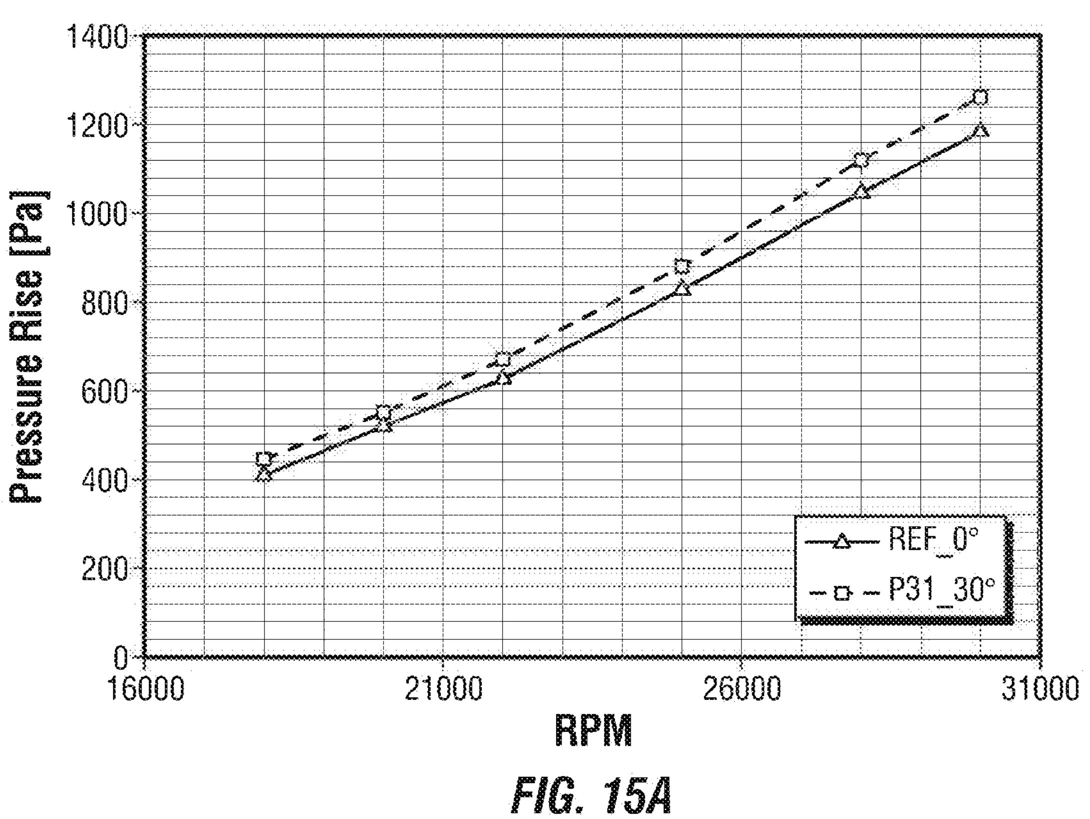
FIGS. 15*a*-15*c* show hydraulic output results, or more particularly, pressure rise, pump flow and shaft relative to rpm for Ref_0 and P31_30.
Figure 15B:
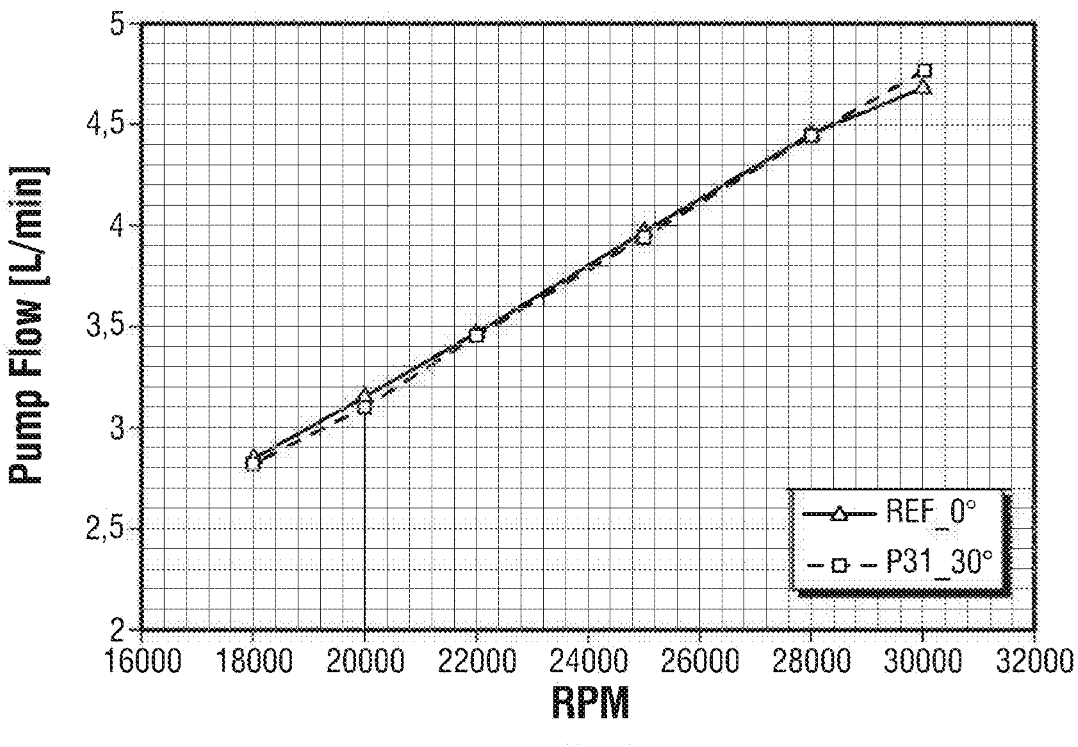
Figure 15C:
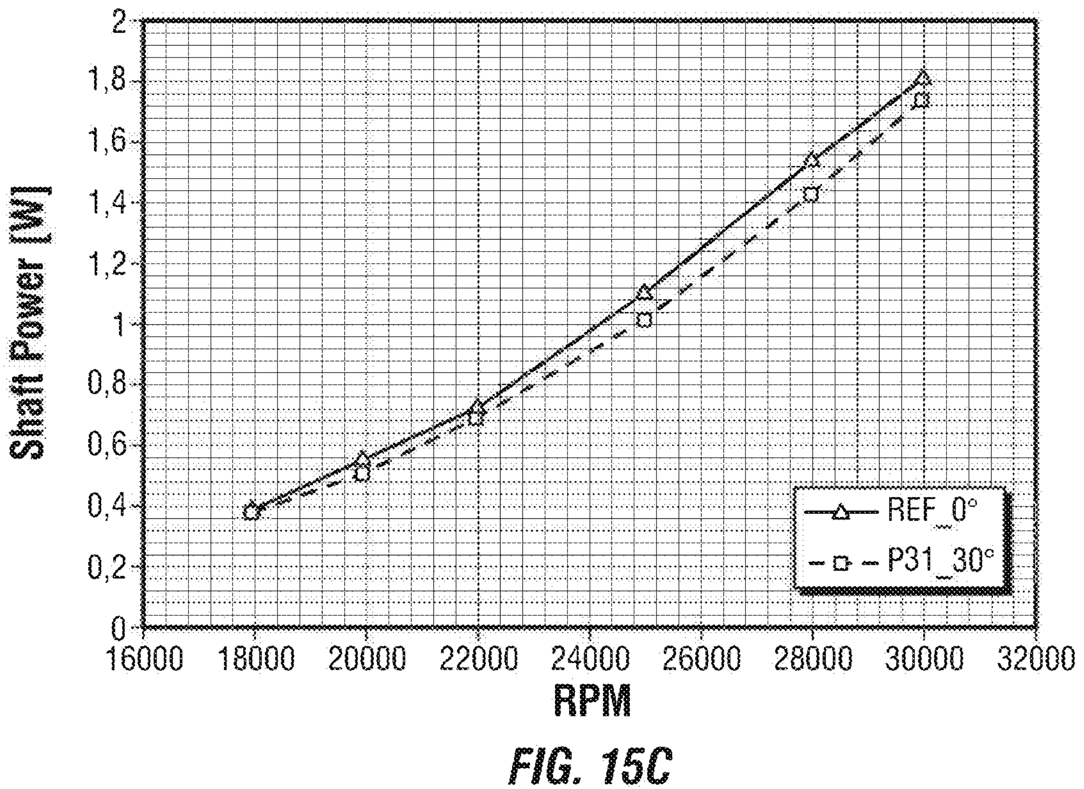

A necessity for any proposed geometry modification in this study is the maintenance of sufficient hydraulic output. The modifications on the impeller blade to achieve a lower hemolytic potential were strictly monitored and compared to the desired hydraulic output. A small increase in hydraulic output was achieved while lowering the necessary impeller shaft power. This yields in an overall better pump efficiency. FIGS. 15*a*-15*c* show hydraulic output results, or more particularly, pressure rise, pump flow and shaft relative to rpm for Ref_0 and P31_30.

Figure 16A:
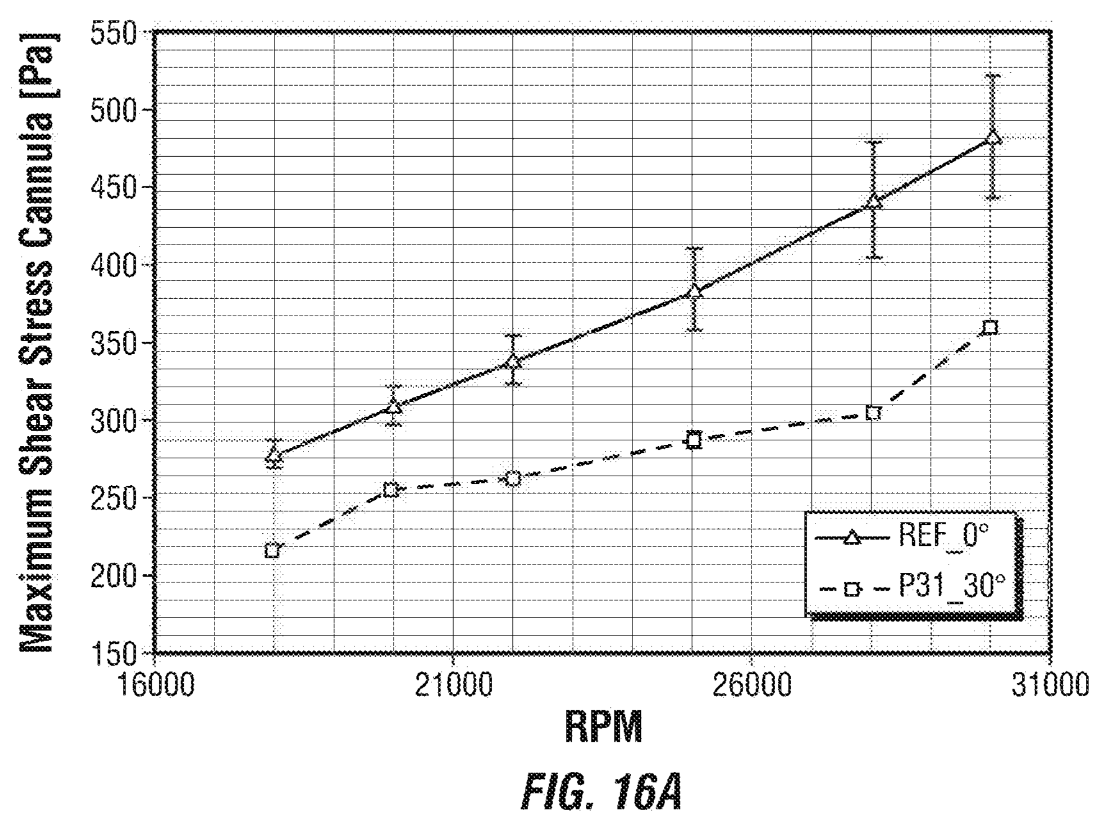
FIGS. 16*a*-16*b* show the maximum and mean shear stress for the reference and P31 design
Figure 16B:
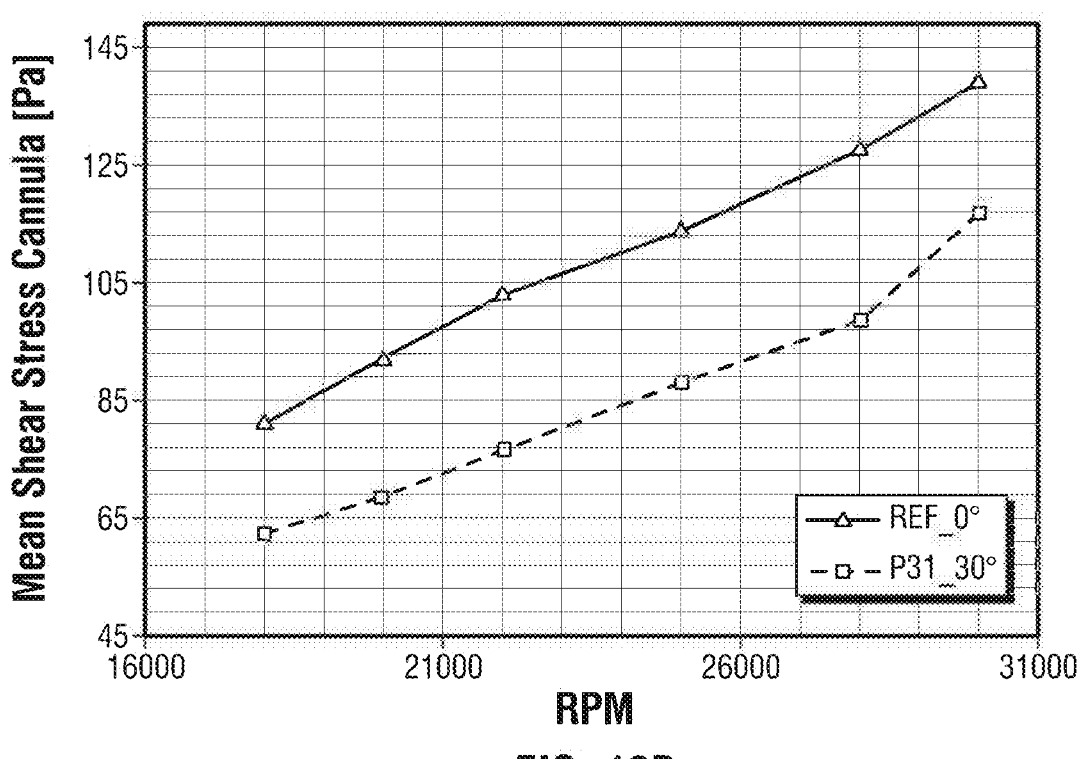

Shroud: The results for the shroud show how both maximum and mean shear stress could be lowered from the reference to the proposed design P31. FIGS. 16*a*-16*b* show the maximum and mean shear stress for the reference and P31 design. A significant offset could be achieved.

It can be argued, that the extension of the shroud also increased the surface area over which the mean values are derived.

Figure 17A:
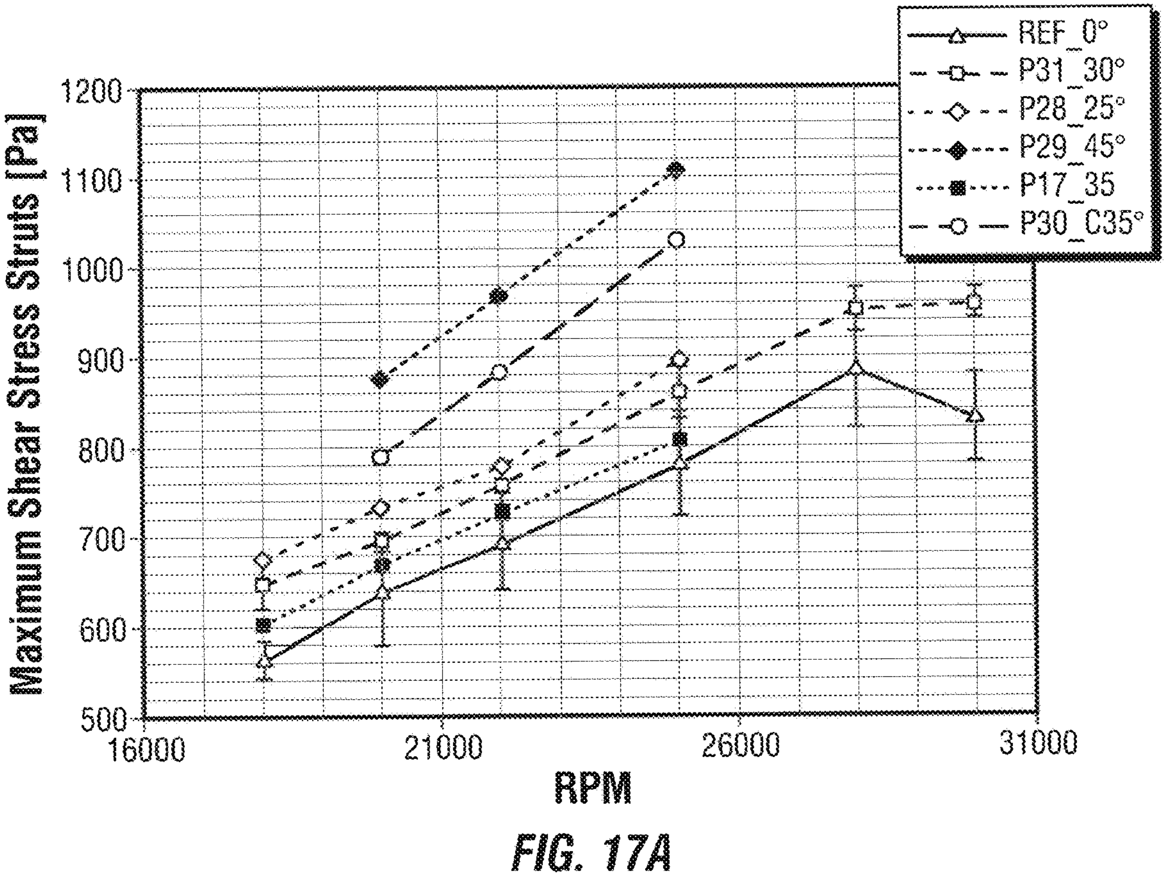
FIGS. 17*a*-17*b* show the maximum and mean shear stress for the reference and P31 design.
Figure 17B:
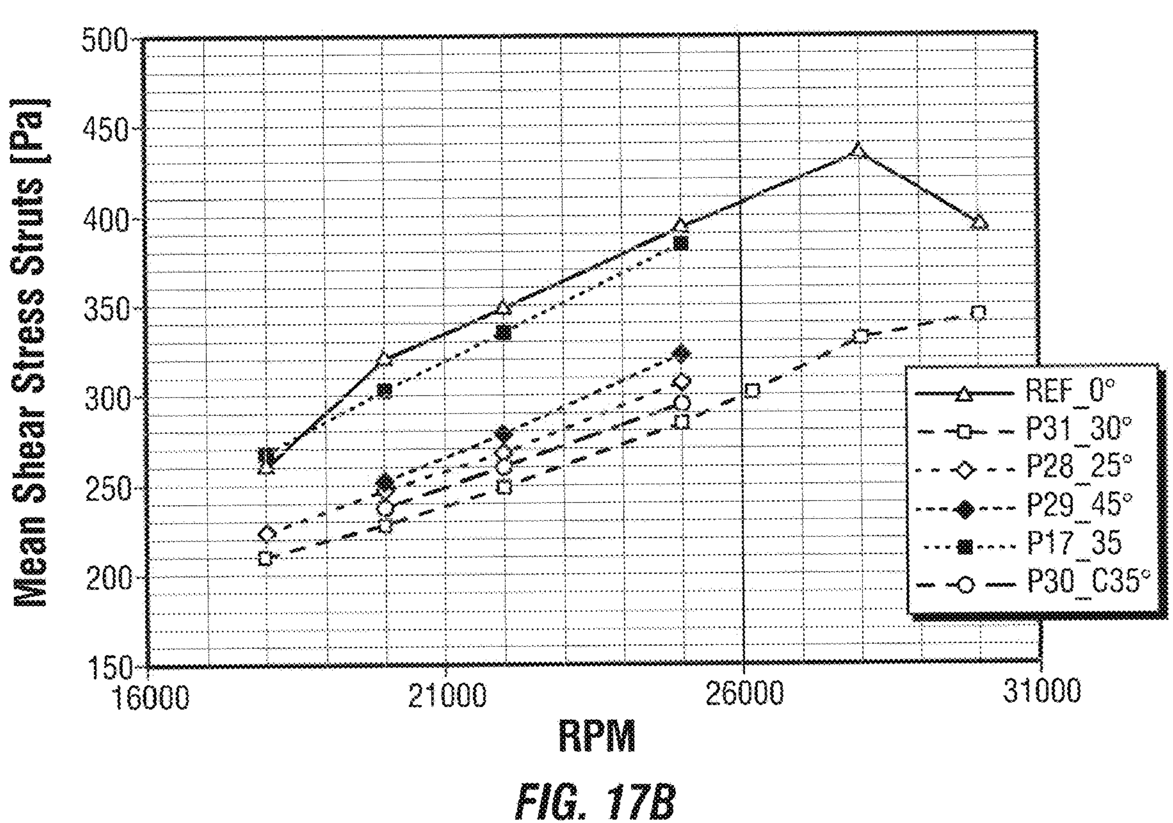
Figure 18A:
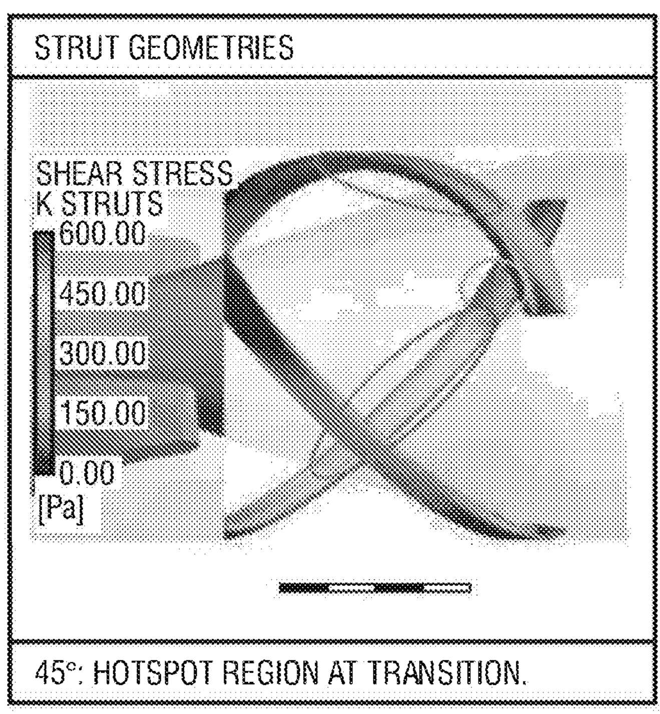
FIGS. 18*a*-18*e* clearly show how the overall mean shear along the pillars could be lowered.
Figure 18B:
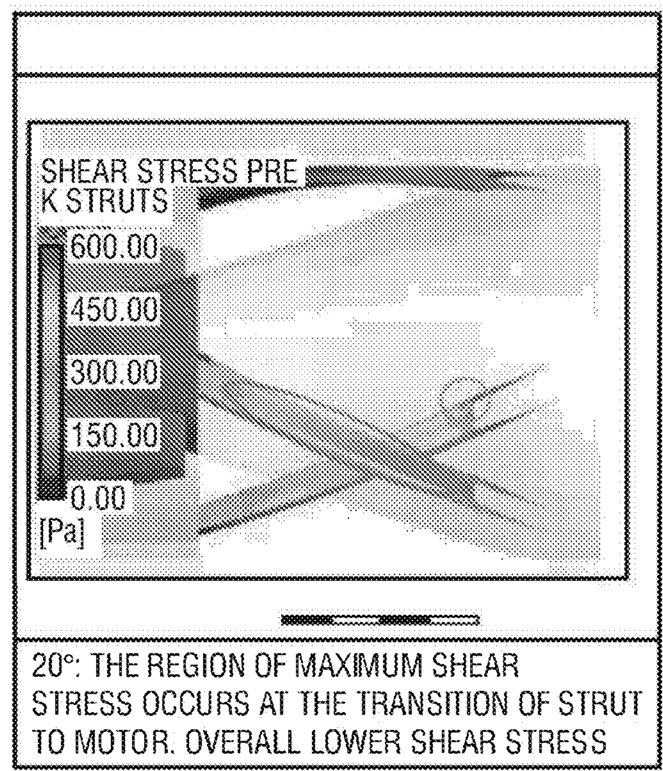
Figure 18C:
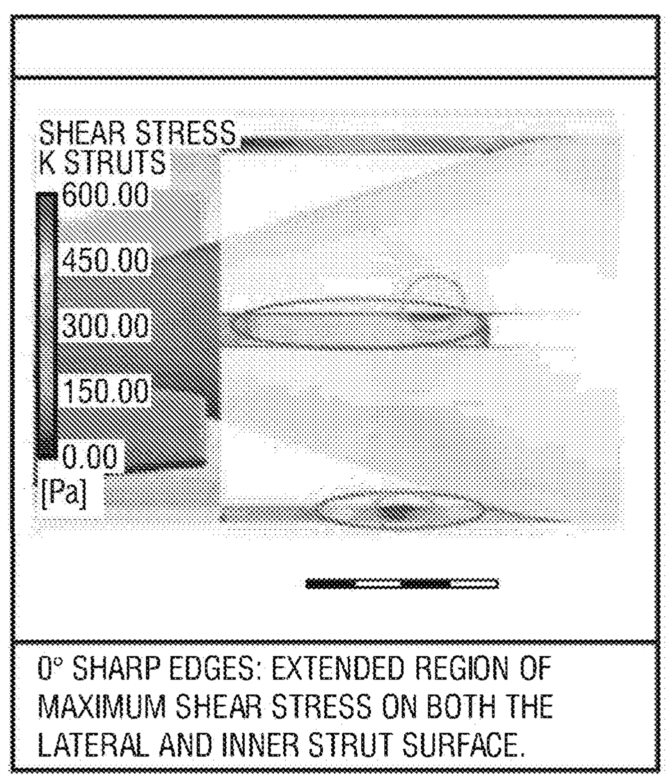
Figure 18D:
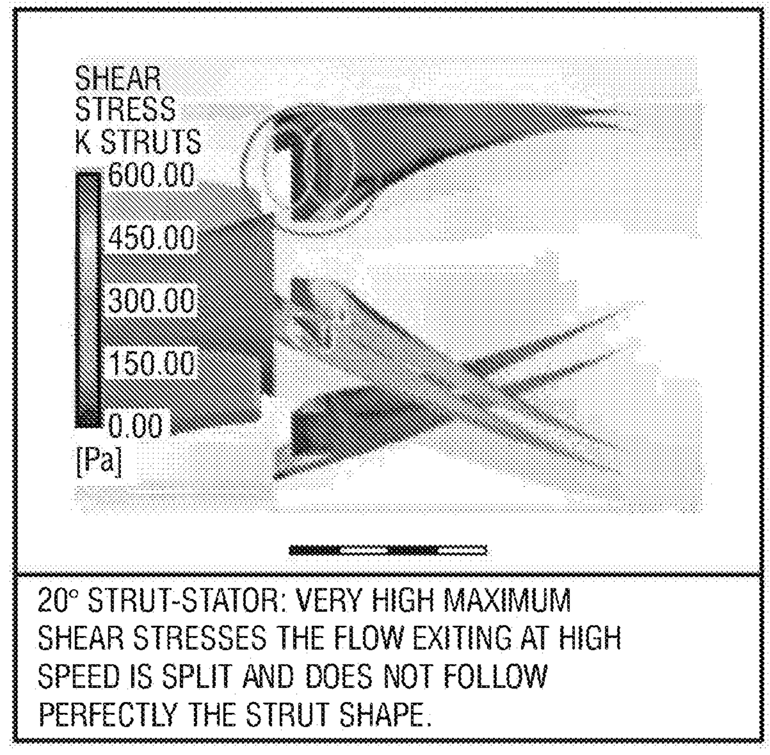
Figure 18E:
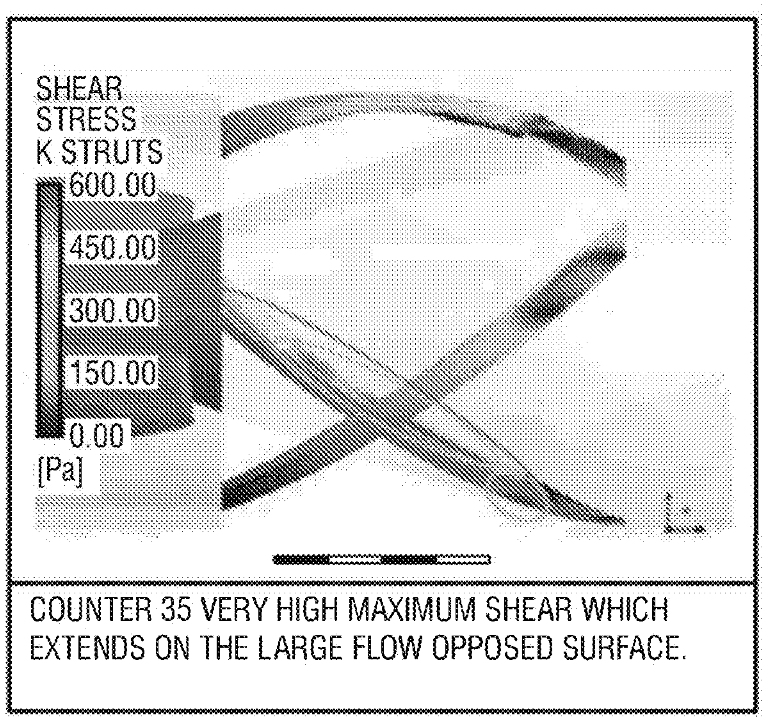

Pillars: FIGS. 17*a*-17*b* show the maximum and mean shear stress for the reference and P31 design. In the case of the pillar analysis the identification of the optimal geometry is not an obvious case. The orientation of the pillars causes higher maximum shear stresses. Comparing the oscillation between P_REF and P_31, it can be seen that through the alignment of the pillars less fluctuating events occurred. At the same time, the flow opposed surface is minimized and the overall mean shear stress could be significantly reduced. The following the trend for P_REF, the straight pillar design might be more beneficial for higher RPM ranges.

The following pictures depict the shear stress distribution at selected pillar geometries. The yellow circle indicates the region of maximum occurring shear while the blue circle covers the region of mean shear.

The charts and FIGS. 18*a*-18*e* clearly show how the overall mean shear along the pillars could be lowered. Best results seem to be feasible with the 30° angle orientation of the pillar geometry.

Impeller

Figure 19A:
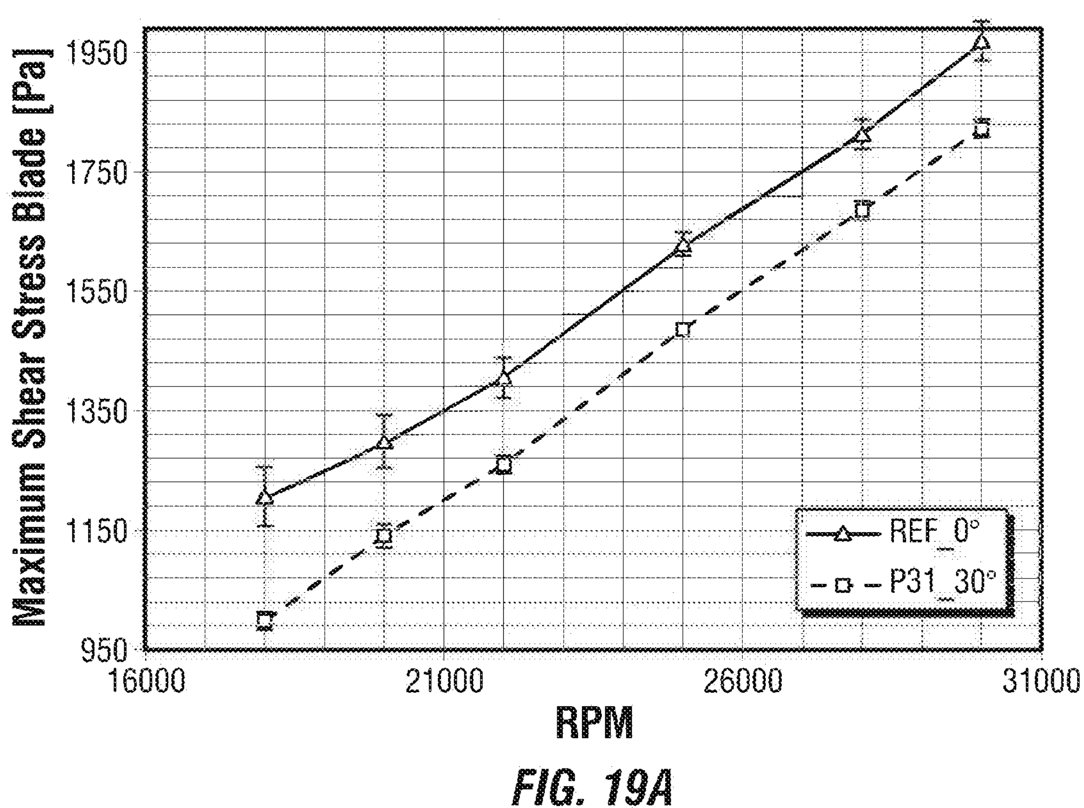
FIGS. 19*a*-19*b* show the maximum and mean shear stress for the reference and P31 design FIG. 20 show Lagrange hemolysis estimations with Heuser constants.
Figures 19B, 20:
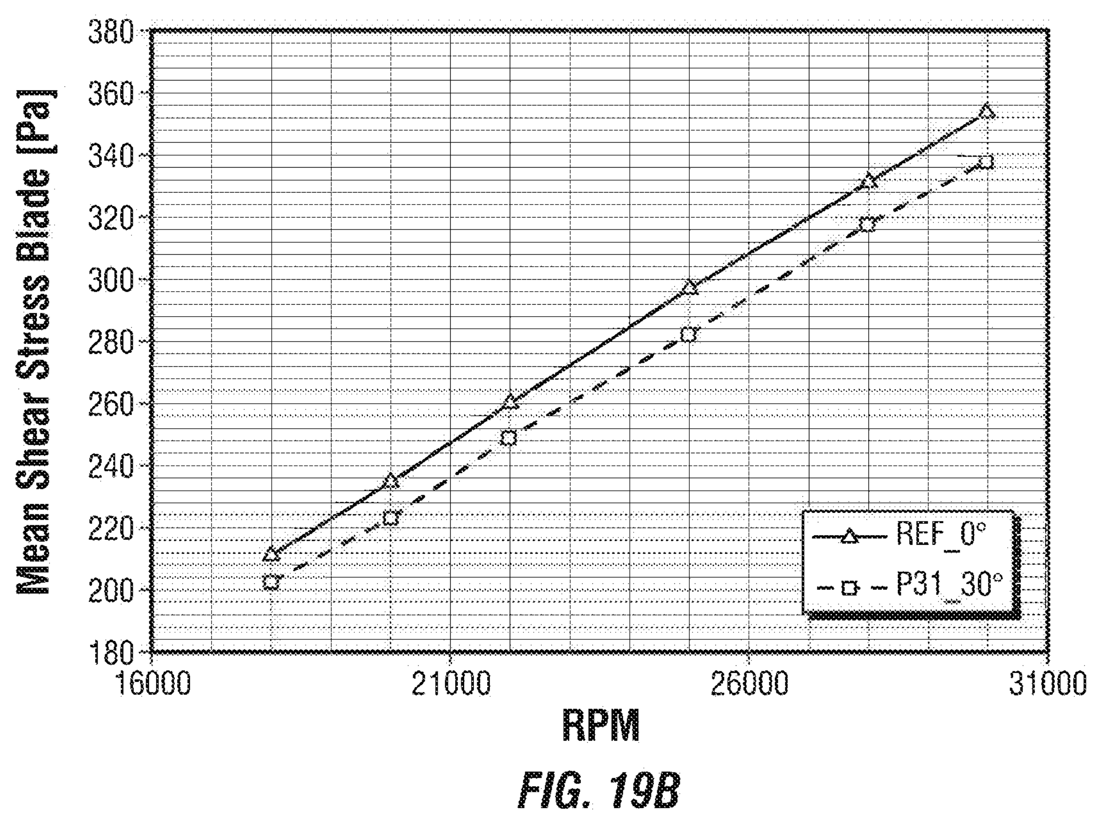

FIGS. 19*a*-19*b* show the maximum and mean shear stress for the reference and P31 design. The extension of the inlet shroud and multiple design iterations including a further extension of the hub (P_17, Milestone1), improved blade angle and wrap angle extent distribution, the inclination of the leading edge (P_22, P_26, P_31) as well as a refined rounding at the impeller leading edge from lead to a consistent offset in both maximum and mean shear stress distribution comparing P_REF to P_31. The extension of shroud could furthermore reduce the impact of detached flow and turbulence on the impeller shear stress distribution and allowed for a refined optimization.

Hemolysis Estimation

The results indicate that high hemolysis is associated with high speed. While the experiments are not an actual representation of actual hemolysis, the experiments do detect significant changes in the geometry that lead to an overall lower shear stress distribution in the blood, and in this case, P_31 shows a lower overall hemolytic potential compared to P_Ref. The accumulation results have to be interpreted in a comparative manner. The absolute values should therefore be understood more qualitatively than quantitatively.

Figure 21:
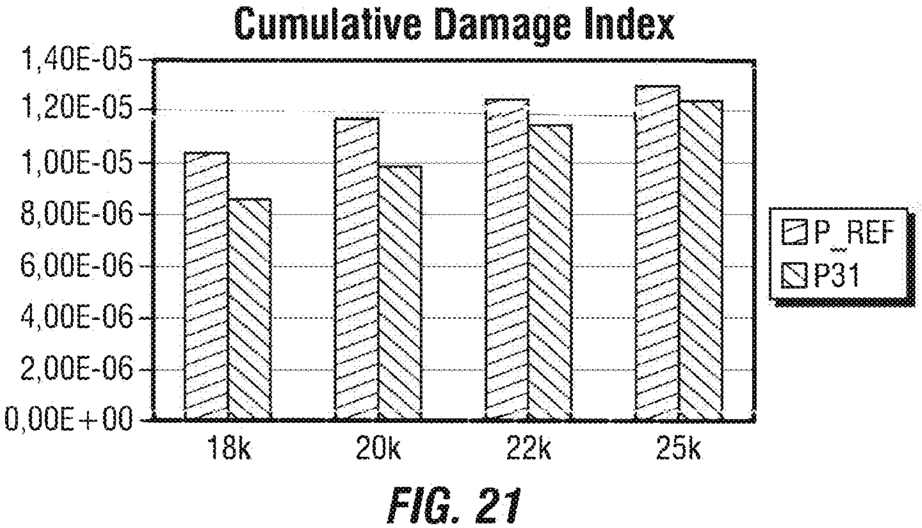
FIG. 21 shows the cumulative damage index for P_Ref and P_31.
Figure 22A:
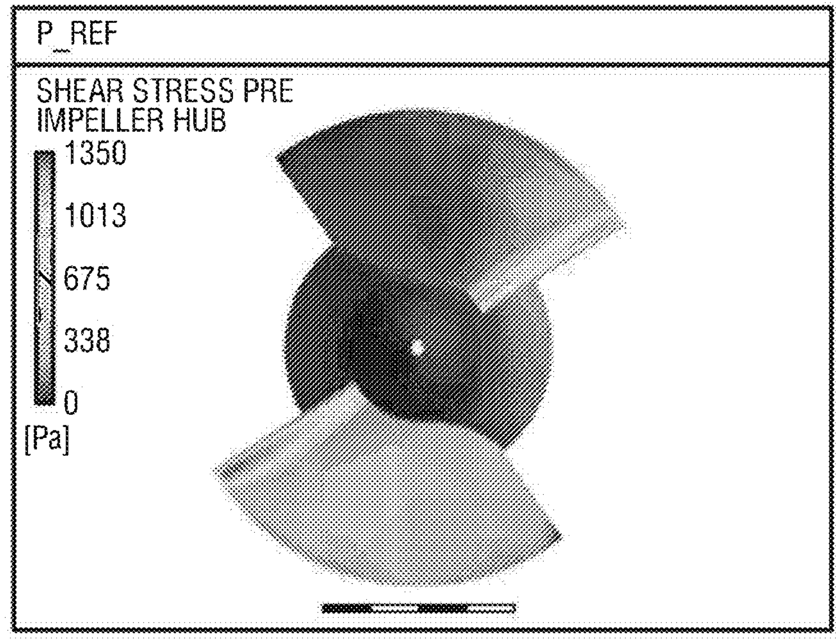
FIGS. 22*a*-22*d* illustrates the changes and improvements in shear reduction made to the impeller from P_ref to the new prototype P_31.
Figure 22B:
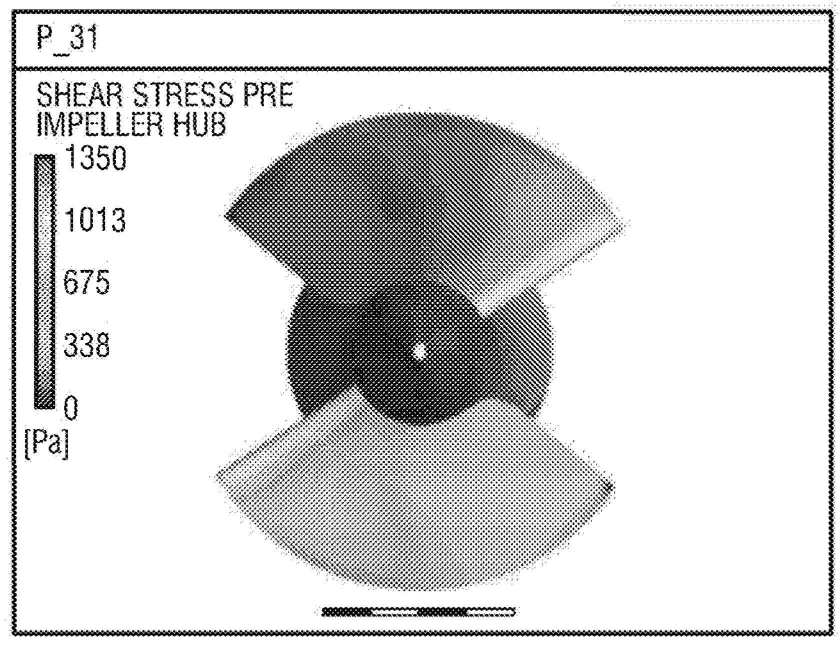
Figure 22C:
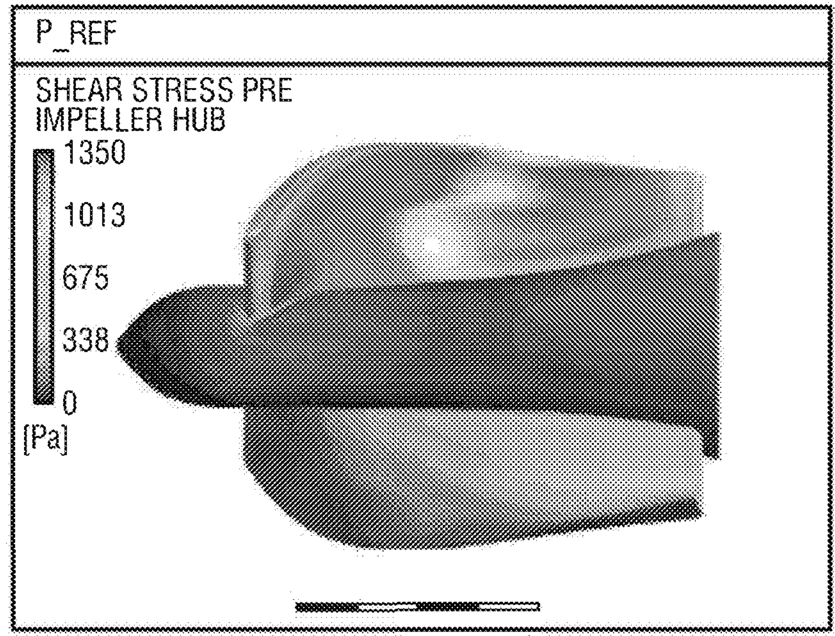
Figure 22D:
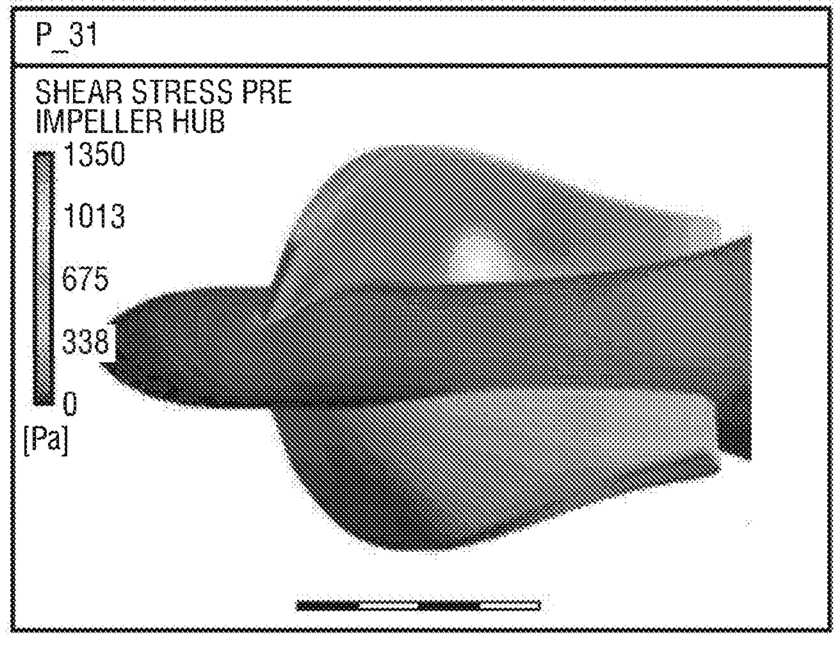

FIG. 20 show Lagrange hemolysis estimations with Heuser constants. FIG. 21 shows the cumulative damage index for P_Ref and P_31.

DISCUSSION

FIGS. 22*a*-22*d* illustrates the changes and improvements in shear reduction made to the impeller from P_ref to the new prototype P_31.

In milestone 1, various hemolysis hotspots were identified and the findings allowed the extension of the current to a more advanced evaluation setup. In milestone 2 of project phase III, 15 individual pump prototypes have been simulated and analyzed over a wide range of pump speeds.

The results of the optimization of the impeller show that a significant reduction of the maximum and mean shear stress for the investigated operational speed range of 18-25 k could be achieved. The combination of impeller P_31 with pillars that are oriented in a 30° angle combined with the proposed extension of inlet shroud proved to be the best combination among the investigated geometries. The overall pump hemolysis contribution has been investigated with a Lagrange particle approach and could furthermore identify a clear improvement. The presented prototype in the current configuration therefore gives raise for a promising perspective for future hemolysis tests.

Figure 23:
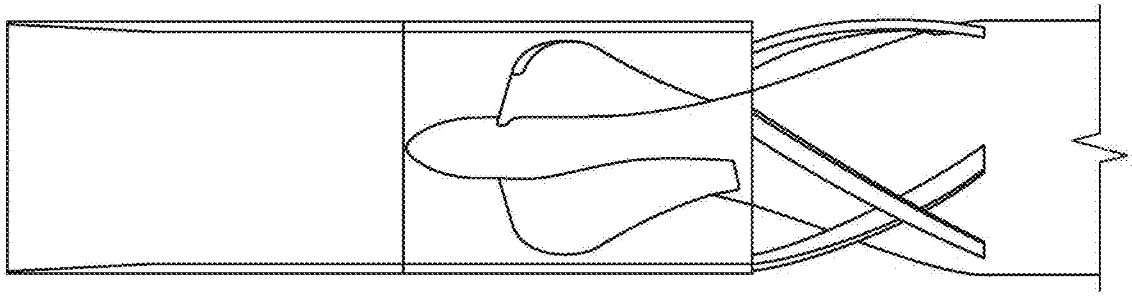
FIG. 23 shows a proposed prototype.

Overall, the results clearly show that additional improvements to the reference impeller were achieved. The new prototype P_31 features lower predicted hemolytic potential, increased efficiency and improved overall flow guidance. FIG. 23 shows a proposed prototype.

Figure 24:
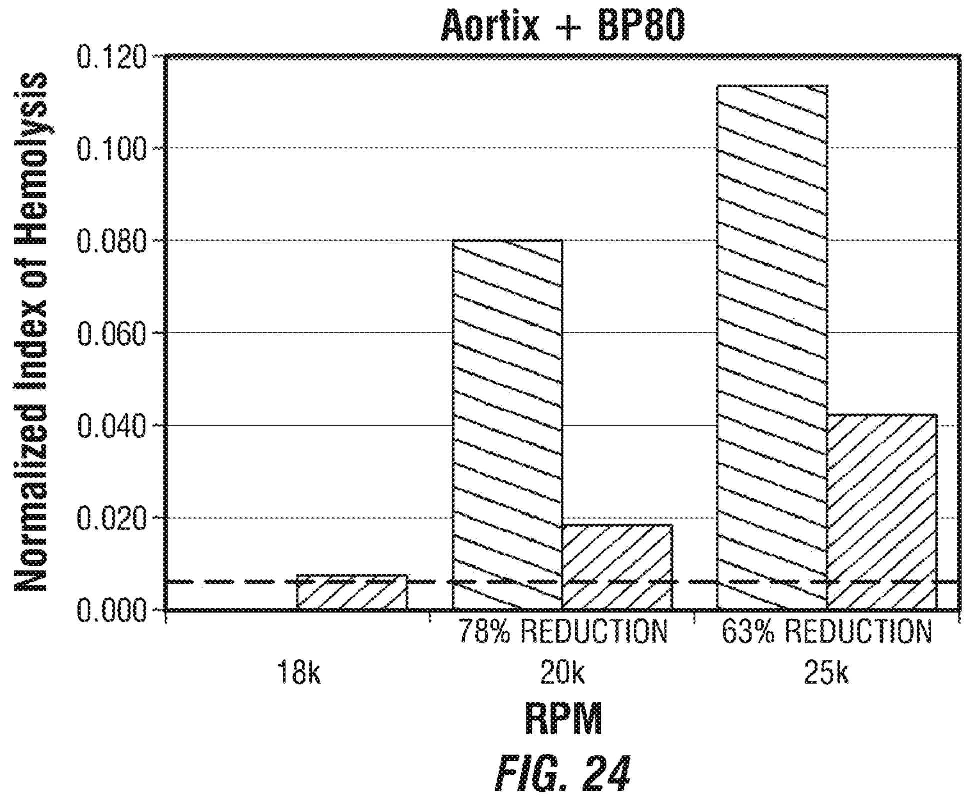
FIG. 24 shows the NIH at various rpm for prototypes.
Figure 25:
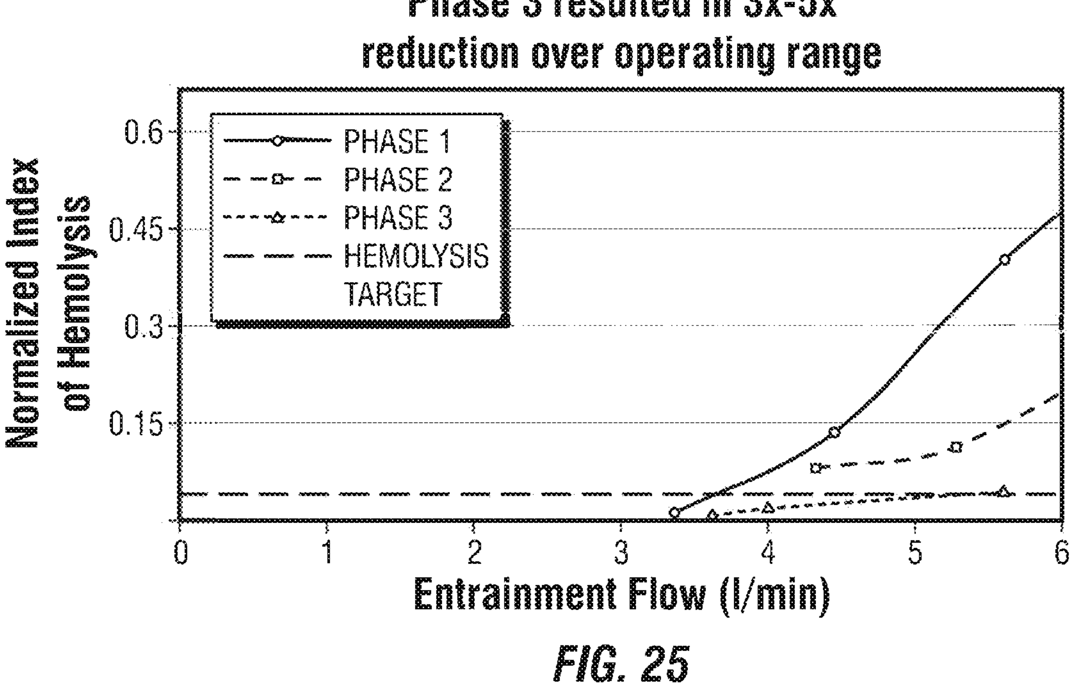
FIG. 25 shows the NIH v. entrainment flow for various phases of testing.

FIG. 24 shows the NIH at various rpm for prototypes. It can be seen from 20 k and 25 k that there are drastic reductions from the improved design. FIG. 25 shows the NIH v. entrainment flow for various phases of testing. It can be seen that that there is a drastic change in the NIH as designs progressed through various prototype phases.

Embodiments described herein are included to demonstrate particular aspects of the present disclosure. It should be appreciated by those of skill in the art that the embodiments described herein merely represent exemplary embodiments of the disclosure. Those of ordinary skill in the art should, in light of the present disclosure, appreciate that many changes can be made in the specific embodiments described and still obtain a like or similar result without departing from the spirit and scope of the present disclosure. From the foregoing description, one of ordinary skill in the art can easily ascertain the essential characteristics of this disclosure, and without departing from the spirit and scope thereof, can make various changes and modifications to adapt the disclosure to various usages and conditions. The embodiments described hereinabove are meant to be illustrative only and should not be taken as limiting of the scope of the disclosure.

What is claimed is:

1. A blood pump having a central axis and comprising:

a shroud comprising an inlet for incoming blood flow, an outlet for outgoing blood flow, a tubular body between the inlet and outlet, and a plurality of pillars extending continuously and proximally from the tubular body non-parallel to the central axis, the shroud comprising an inner circumferential surface at least partially defined by the tubular body and the plurality of pillars, the inner circumferential surface and an opposite outer circumferential surface being spaced apart by a thickness of the shroud, each pillar extending between a first end connected with the tubular body and a second end, wherein at least a portion of the pillar between the first and second ends is spaced apart from the impeller and the proximal body portion by a gap;

an impeller having a blade disposed within the tubular body of the shroud and extending generally along the central axis, the inner circumferential surface of the shroud facing the impeller, the thickness of the shroud being less than a length of the blade;

a body extending proximally from the impeller, the body comprising an outer surface having a first portion angled relative to the central axis and a second portion generally parallel to the central axis, at least part of the first portion aligned with the outlet along the central axis.

2. The blood pump of claim 1, wherein the body comprises a motor, the motor configured to impart rotation to the impeller.

3. The blood pump of claim 2, wherein the motor comprises a motor body and a stator, the stator disposed between the impeller and the motor body.

4. The blood pump of claim 3, wherein at least part of the second portion is aligned with the outlet along the central axis.

5. The blood pump of claim 3, wherein a first pillar of the plurality of pillars has a first end coupled with a proximal portion of the tubular body at the outlet of the shroud.

6. The pump of claim 5, wherein the second end of the first pillar is connected to a portion of the shroud proximal the stator.

7. The pump of claim 5, wherein the plurality of pillars are disposed about an outer periphery of the impeller, the plurality of pillars comprising the first pillar.

8. The blood pump of claim 1, wherein the impeller comprises a plurality of blades including the blade.

9. The blood pump of claim 1, wherein a size of the inlet is larger than a size of the outlet.

10. The blood pump of claim 1, further comprising a strut extending distally and radially outwardly of the inlet of the shroud non-parallel to the central axis.

11. The blood pump of claim 10, wherein the strut comprises an angled distal end portion, and wherein the angled distal end portion comprises a bend at a distal-most end of the strut.

12. The blood pump of claim 10, further comprising a plurality of struts including the strut.

13. A blood pump having a central axis and comprising:

a shroud comprising an inlet for incoming blood flow, an outlet for outgoing blood flow, a tubular body between the inlet and outlet, and a plurality of pillars extending from the tubular body non-parallel to the central axis, the shroud comprising an inner circumferential surface at least partially defined by the tubular body and the plurality of pillars, the inner circumferential surface and an opposite outer circumferential surface being spaced apart by a thickness of the shroud, each pillar extending proximally of the tubular body along the outlet, wherein at least a portion of a length of the pillar between the first and second ends is spaced apart from the impeller and the proximal body portion by a gap;

an impeller having a blade disposed within the tubular body of the shroud and extending generally along the central axis, the inner circumferential surface of the shroud facing the impeller, the thickness of the shroud being less than a length of the blade; and a body extending proximally from the impeller, the body comprising an outer surface being disposed at or radially inwards of a straight line intersecting a distal end and a proximal end of the outer surface.

14. The blood pump of claim 13, wherein the body comprises a motor, the motor configured to impart rotation to the impeller.

15. The blood pump of claim 14, wherein the motor comprises a motor body and a stator, the stator disposed between the impeller and the motor body.

16. The blood pump of claim 13, wherein the impeller comprises a plurality of blades including the blade.

17. The blood pump of claim 13, wherein a size of the inlet is larger than a size of the outlet.

18. The blood pump of claim 13, further comprising a strut extending distally and radially outwardly of the inlet of the shroud non-parallel to the central axis.

19. The blood pump of claim 18, wherein the strut comprises an angled distal end portion, and wherein the angled distal end portion comprises a bend at a distal-most end of the strut.

20. The blood pump of claim 18, further comprising a plurality of struts including the strut.

* * * * *